US008755820B2

(12) United States Patent
Huber et al.

(10) Patent No.: US 8,755,820 B2
(45) Date of Patent: *Jun. 17, 2014

(54) LOCATION-BASED SERVICES IN A FEMTOCELL NETWORK

(71) Applicant: AT&T Mobility II LLC, Atlanta, GA (US)

(72) Inventors: Kurt Donald Huber, Coral Springs, FL (US); William Gordon Mansfield, Sugar Hill, GA (US); Judson John Flynn, Decatur, GA (US)

(73) Assignee: AT&T Mobility II LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/892,923

(22) Filed: May 13, 2013

(65) Prior Publication Data

US 2013/0252632 A1 Sep. 26, 2013

Related U.S. Application Data

(63) Continuation of application No. 13/487,794, filed on Jun. 4, 2012, now Pat. No. 8,463,296, which is a continuation of application No. 12/465,483, filed on May 13, 2009, now Pat. No. 8,219,094.

(60) Provisional application No. 61/052,813, filed on May 13, 2008.

(51) Int. Cl.
*H04W 4/02* (2009.01)

(52) U.S. Cl.
USPC .......... 455/456.1; 455/450; 455/444

(58) Field of Classification Search
USPC .......... 455/456.1–456.6
See application file for complete search history.

(56) References Cited

U.S. PATENT DOCUMENTS 5,745,559 A 4/1998 Weir
5,864,764 A 1/1999 Thro et al.
(Continued)

FOREIGN PATENT DOCUMENTS

CN 101017554 A 8/2007
CN 101175333 A 5/2008
(Continued)

OTHER PUBLICATIONS

Canadian Office Action mailed Mar. 26, 2013 for Canadian Patent Application No. 2,722,324,4 pages.
(Continued)

*Primary Examiner* — Kashif Siddiqui
(74) *Attorney, Agent, or Firm* — Amin, Turocy & Watson, LLP

(57) ABSTRACT

Traffic and signaling are routed between a set of networked femto access points (APs) and location-based services are enabled. A femto AP in the set of femto APs is functionally linked to a routing platform that manages traffic and signaling, and is functionally connected to a controller component that relays at least part of data and control to a femto network platform. The femto network platform allows access to one or more external networks. Routing platform can exchange signaling with one or more femto APs to enable, at least in part, location-based services based at least in part on identifier(s) for a femto AP, access privileges, or time-of-flight measurements that assess propagation timing between a mobile device and a femto AP. Routing platform can supply timing configuration to enable predetermined spatial resolution of location estimates. Location estimates can be recorded and conveyed to a consumer layer.

20 Claims, 21 Drawing Sheets

(56) References Cited

U.S. PATENT DOCUMENTS

| | | | |
|---|---|---|---|
| 6,052,594 A | 4/2000 | Chuang et al. | |
| 6,151,505 A | 11/2000 | Larkins | |
| 6,208,659 B1 | 3/2001 | Govindarajan et al. | |
| 6,219,786 B1 | 4/2001 | Cunningham et al. | |
| 6,256,504 B1 | 7/2001 | Tell et al. | |
| 6,266,537 B1 | 7/2001 | Kashitani et al. | |
| 6,295,454 B1 * | 9/2001 | Havinis et al. | 455/456.3 |
| 6,363,261 B1 | 3/2002 | Raghavan | |
| 6,483,852 B1 | 11/2002 | Jacquet et al. | |
| 6,484,096 B2 | 11/2002 | Wong | |
| 6,512,478 B1 | 1/2003 | Chien | |
| 6,710,651 B2 | 3/2004 | Forrester | |
| 6,718,023 B1 | 4/2004 | Zolotov | |
| 6,768,722 B1 | 7/2004 | Katseff et al. | |
| 7,080,139 B1 | 7/2006 | Briggs et al. | |
| 7,142,861 B2 | 11/2006 | Murai | |
| 7,146,153 B2 | 12/2006 | Russell | |
| 7,209,739 B1 | 4/2007 | Narayanabhatla | |
| 7,277,410 B2 | 10/2007 | Horneman | |
| 7,317,931 B2 | 1/2008 | Guo | |
| 7,370,356 B1 | 5/2008 | Guo | |
| 7,437,755 B2 | 10/2008 | Farino et al. | |
| 7,493,390 B2 | 2/2009 | Bobde et al. | |
| 7,496,383 B2 | 2/2009 | Kurata | |
| 7,509,124 B2 | 3/2009 | O'Neil | |
| 7,516,219 B2 | 4/2009 | Moghaddam et al. | |
| 7,558,251 B1 | 7/2009 | Huang et al. | |
| 7,574,731 B2 | 8/2009 | Fascenda | |
| 7,613,444 B2 | 11/2009 | Lindqvist et al. | |
| 7,614,078 B1 | 11/2009 | Stieglitz et al. | |
| 7,623,857 B1 | 11/2009 | O'Neil | |
| 7,633,910 B2 | 12/2009 | Zhun et al. | |
| 7,751,826 B2 | 7/2010 | Gardner | |
| 7,761,526 B2 | 7/2010 | Pounds et al. | |
| 7,768,983 B2 | 8/2010 | Nylander et al. | |
| 7,853,265 B1 | 12/2010 | Ahmad et al. | |
| 7,885,644 B2 | 2/2011 | Gallagher et al. | |
| 7,929,537 B2 | 4/2011 | Vasudevan et al. | |
| 7,929,970 B1 | 4/2011 | Gunasekara | |
| 7,941,144 B2 | 5/2011 | Nylander et al. | |
| 7,995,994 B2 | 8/2011 | Khetawat et al. | |
| 8,064,909 B2 | 11/2011 | Spinelli et al. | |
| 8,103,285 B2 * | 1/2012 | Kalhan | 455/456.1 |
| 8,108,923 B1 | 1/2012 | Satish et al. | |
| 8,437,745 B2 | 5/2013 | Theppasaandra et al. | |
| 2002/0044639 A1 | 4/2002 | Shioda et al. | |
| 2002/0077115 A1 * | 6/2002 | Ruutu et al. | 455/456 |
| 2002/0098837 A1 | 7/2002 | Ferrario et al. | |
| 2002/0107018 A1 | 8/2002 | Nakamura et al. | |
| 2002/0123365 A1 | 9/2002 | Thorson | |
| 2002/0142791 A1 | 10/2002 | Chen et al. | |
| 2003/0028621 A1 | 2/2003 | Furlong et al. | |
| 2003/0109271 A1 | 6/2003 | Lewis et al. | |
| 2003/0125044 A1 | 7/2003 | Deloach | |
| 2003/0133558 A1 | 7/2003 | Kung et al. | |
| 2003/0139180 A1 | 7/2003 | McIntosh et al. | |
| 2003/0142637 A1 | 7/2003 | Khawer et al. | |
| 2003/0144793 A1 | 7/2003 | Melaku et al. | |
| 2003/0153302 A1 | 8/2003 | Lewis et al. | |
| 2004/0111382 A1 | 6/2004 | Haji-Ioannou | |
| 2004/0125781 A1 | 7/2004 | Walter et al. | |
| 2004/0203846 A1 | 10/2004 | Caronni et al. | |
| 2004/0235455 A1 | 11/2004 | Jiang | |
| 2004/0236702 A1 | 11/2004 | Fink et al. | |
| 2004/0258003 A1 | 12/2004 | Kokot et al. | |
| 2004/0264428 A1 | 12/2004 | Choi et al. | |
| 2005/0003797 A1 | 1/2005 | Baldwin | |
| 2005/0009499 A1 | 1/2005 | Koster | |
| 2005/0024201 A1 * | 2/2005 | Culpepper et al. | 340/539.13 |
| 2005/0026650 A1 | 2/2005 | Russell | |
| 2005/0075114 A1 | 4/2005 | Dennison et al. | |
| 2005/0108529 A1 | 5/2005 | Juneau | |
| 2005/0144279 A1 | 6/2005 | Wexelblat | |
| 2005/0160276 A1 | 7/2005 | Braun et al. | |
| 2005/0172148 A1 | 8/2005 | Ying | |
| 2005/0177645 A1 | 8/2005 | Dowling et al. | |
| 2005/0223389 A1 | 10/2005 | Klein et al. | |
| 2005/0239448 A1 | 10/2005 | Bayne | |
| 2005/0250527 A1 | 11/2005 | Jugl | |
| 2005/0254451 A1 | 11/2005 | Grosbach | |
| 2005/0255893 A1 | 11/2005 | Jin et al. | |
| 2005/0259654 A1 | 11/2005 | Faulk, Jr. | |
| 2005/0269402 A1 | 12/2005 | Spitzer et al. | |
| 2005/0283518 A1 | 12/2005 | Sargent | |
| 2006/0031387 A1 | 2/2006 | Hamzeh et al. | |
| 2006/0031493 A1 | 2/2006 | Cugi | |
| 2006/0046647 A1 | 3/2006 | Parikh et al. | |
| 2006/0074814 A1 | 4/2006 | Lovell et al. | |
| 2006/0075098 A1 | 4/2006 | Becker et al. | |
| 2006/0182074 A1 | 8/2006 | Kubler et al. | |
| 2006/0223498 A1 | 10/2006 | Gallagher et al. | |
| 2006/0244589 A1 | 11/2006 | Schranz | |
| 2006/0281457 A1 | 12/2006 | Huotari et al. | |
| 2007/0002844 A1 | 1/2007 | Ali | |
| 2007/0008894 A1 | 1/2007 | Lynch et al. | |
| 2007/0025245 A1 | 2/2007 | Porras et al. | |
| 2007/0032225 A1 | 2/2007 | Konicek et al. | |
| 2007/0032269 A1 | 2/2007 | Shostak | |
| 2007/0066318 A1 | 3/2007 | Danzeisen et al. | |
| 2007/0074272 A1 | 3/2007 | Watanabe | |
| 2007/0094601 A1 | 4/2007 | Greenberg et al. | |
| 2007/0097093 A1 | 5/2007 | Ohshita et al. | |
| 2007/0097938 A1 | 5/2007 | Nylander et al. | |
| 2007/0097939 A1 | 5/2007 | Nylander et al. | |
| 2007/0097983 A1 | 5/2007 | Nylander et al. | |
| 2007/0099561 A1 | 5/2007 | Voss | |
| 2007/0104166 A1 | 5/2007 | Rahman et al. | |
| 2007/0111706 A1 | 5/2007 | Kumar et al. | |
| 2007/0123253 A1 | 5/2007 | Simongini et al. | |
| 2007/0124802 A1 | 5/2007 | Anton et al. | |
| 2007/0133563 A1 | 6/2007 | Hundscheidt et al. | |
| 2007/0150732 A1 | 6/2007 | Suzuki et al. | |
| 2007/0155421 A1 | 7/2007 | Alberth et al. | |
| 2007/0167175 A1 | 7/2007 | Wong | |
| 2007/0183427 A1 | 8/2007 | Nylander et al. | |
| 2007/0184815 A1 | 8/2007 | Aebi | |
| 2007/0199076 A1 | 8/2007 | Rensin et al. | |
| 2007/0220252 A1 | 9/2007 | Sinko et al. | |
| 2007/0232332 A1 | 10/2007 | Holur et al. | |
| 2007/0258418 A1 | 11/2007 | Wurtenberger et al. | |
| 2007/0270152 A1 | 11/2007 | Nylander et al. | |
| 2007/0275739 A1 | 11/2007 | Blackburn | |
| 2007/0287501 A1 | 12/2007 | Hoshina | |
| 2008/0043972 A1 | 2/2008 | Ruetschi et al. | |
| 2008/0049702 A1 | 2/2008 | Meylan et al. | |
| 2008/0065752 A1 | 3/2008 | Ch'ng et al. | |
| 2008/0076392 A1 | 3/2008 | Khetawat et al. | |
| 2008/0076393 A1 | 3/2008 | Khetawat et al. | |
| 2008/0076398 A1 | 3/2008 | Mate et al. | |
| 2008/0076412 A1 | 3/2008 | Khetawat et al. | |
| 2008/0076419 A1 | 3/2008 | Khetawat et al. | |
| 2008/0076420 A1 | 3/2008 | Khetawat et al. | |
| 2008/0076425 A1 | 3/2008 | Khetawat et al. | |
| 2008/0081636 A1 | 4/2008 | Nylander et al. | |
| 2008/0082538 A1 | 4/2008 | Meijer et al. | |
| 2008/0119160 A1 | 5/2008 | Andriantsiferana et al. | |
| 2008/0126531 A1 | 5/2008 | Setia et al. | |
| 2008/0132239 A1 | 6/2008 | Khetawat et al. | |
| 2008/0133742 A1 | 6/2008 | Southiere et al. | |
| 2008/0141348 A1 | 6/2008 | Hovnanian et al. | |
| 2008/0151807 A1 | 6/2008 | Meier et al. | |
| 2008/0168099 A1 | 7/2008 | Skaf | |
| 2008/0181184 A1 | 7/2008 | Kezys | |
| 2008/0201076 A1 | 8/2008 | Huang et al. | |
| 2008/0207170 A1 | 8/2008 | Khetawat et al. | |
| 2008/0242280 A1 | 10/2008 | Shapiro et al. | |
| 2008/0244148 A1 | 10/2008 | Nix et al. | |
| 2008/0254792 A1 | 10/2008 | Ch'ng | |
| 2008/0261602 A1 | 10/2008 | Livneh | |
| 2008/0274753 A1 * | 11/2008 | Attar et al. | 455/456.6 |
| 2008/0281687 A1 | 11/2008 | Hurwitz et al. | |
| 2008/0282327 A1 | 11/2008 | Winget et al. | |
| 2008/0299984 A1 | 12/2008 | Shimomura | |
| 2008/0299992 A1 | 12/2008 | Eitan et al. | |

(56) References Cited

U.S. PATENT DOCUMENTS

| | | |
|---|---|---|
| 2008/0305792 A1 | 12/2008 | Khetawat et al. |
| 2008/0305801 A1 | 12/2008 | Burgess et al. |
| 2008/0305834 A1 | 12/2008 | Janiszewski et al. |
| 2008/0318551 A1 | 12/2008 | Palamara et al. |
| 2009/0012898 A1 | 1/2009 | Sharma et al. |
| 2009/0031006 A1 | 1/2009 | Johnson et al. |
| 2009/0037973 A1 | 2/2009 | Gustave et al. |
| 2009/0042593 A1 | 2/2009 | Yavuz et al. |
| 2009/0046665 A1 | 2/2009 | Robson et al. |
| 2009/0047945 A1 | 2/2009 | Zhang |
| 2009/0059822 A1 | 3/2009 | Morrill et al. |
| 2009/0061821 A1 | 3/2009 | Chen et al. |
| 2009/0061873 A1 | 3/2009 | Bao et al. |
| 2009/0077620 A1 | 3/2009 | Ravi et al. |
| 2009/0082010 A1 | 3/2009 | Lee |
| 2009/0082020 A1 | 3/2009 | Ch'ng et al. |
| 2009/0092080 A1 | 4/2009 | Balasubramanian et al. |
| 2009/0092081 A1 | 4/2009 | Balasubramanian et al. |
| 2009/0092096 A1 | 4/2009 | Czaja |
| 2009/0092097 A1 | 4/2009 | Nylander et al. |
| 2009/0093232 A1 | 4/2009 | Gupta et al. |
| 2009/0094351 A1 | 4/2009 | Gupta et al. |
| 2009/0094680 A1 | 4/2009 | Gupta et al. |
| 2009/0097436 A1 | 4/2009 | Vasudevan et al. |
| 2009/0098871 A1 | 4/2009 | Gogic |
| 2009/0111499 A1 | 4/2009 | Bosch |
| 2009/0122773 A1 | 5/2009 | Gogic |
| 2009/0124262 A1 | 5/2009 | Vela et al. |
| 2009/0129336 A1 | 5/2009 | Osborn et al. |
| 2009/0129350 A1 | 5/2009 | Khandekar et al. |
| 2009/0131050 A1 | 5/2009 | Osborn |
| 2009/0131098 A1 | 5/2009 | Khandekar et al. |
| 2009/0135749 A1 | 5/2009 | Yang |
| 2009/0135794 A1 | 5/2009 | Su et al. |
| 2009/0156213 A1 | 6/2009 | Spinelli et al. |
| 2009/0161682 A1 | 6/2009 | Johnson et al. |
| 2009/0163216 A1* | 6/2009 | Hoang et al. ............... 455/450 |
| 2009/0163224 A1 | 6/2009 | Dean |
| 2009/0164547 A1 | 6/2009 | Ch'ng et al. |
| 2009/0170440 A1 | 7/2009 | Eyuboglu et al. |
| 2009/0170528 A1 | 7/2009 | Bull et al. |
| 2009/0180428 A1 | 7/2009 | Viswanath |
| 2009/0191844 A1 | 7/2009 | Morgan et al. |
| 2009/0191845 A1 | 7/2009 | Morgan et al. |
| 2009/0210324 A1 | 8/2009 | Bhogal |
| 2009/0213825 A1 | 8/2009 | Gupta et al. |
| 2009/0215429 A1 | 8/2009 | Caldwell et al. |
| 2009/0215452 A1 | 8/2009 | Balasubramanian et al. |
| 2009/0221303 A1 | 9/2009 | Soliman |
| 2009/0233574 A1 | 9/2009 | Shinozaki |
| 2009/0245176 A1 | 10/2009 | Balasubramanian et al. |
| 2009/0253421 A1 | 10/2009 | Camp et al. |
| 2009/0253432 A1 | 10/2009 | Willey et al. |
| 2009/0257434 A1 | 10/2009 | Song et al. |
| 2009/0279701 A1 | 11/2009 | Moisand et al. |
| 2009/0291667 A1 | 11/2009 | Vakil et al. |
| 2009/0325634 A1 | 12/2009 | Bienas et al. |
| 2010/0022266 A1 | 1/2010 | Villier |
| 2010/0040026 A1 | 2/2010 | Melkesetian |
| 2010/0048165 A1 | 2/2010 | Caldwell et al. |
| 2010/0113067 A1 | 5/2010 | Fullam et al. |
| 2010/0167777 A1 | 7/2010 | Raghothaman et al. |
| 2010/0260068 A1 | 10/2010 | Bhatt et al. |
| 2011/0177794 A1 | 7/2011 | Nylander et al. |
| 2011/0200022 A1 | 8/2011 | Annamalai |
| 2011/0280154 A1 | 11/2011 | Silverstrim et al. |

FOREIGN PATENT DOCUMENTS

| | | |
|---|---|---|
| GB | 2425291 A | 10/2006 |
| GB | 2425921 A | 11/2006 |
| JP | 20010264096 | 9/2001 |
| JP | 2003022303 | 1/2003 |
| JP | 2003088521 | 10/2003 |
| JP | 2004112324 | 4/2004 |
| JP | 2005073147 | 3/2005 |
| JP | 2005215849 | 8/2005 |
| JP | 20060674143 | 3/2006 |
| JP | 2008048055 | 2/2008 |
| WO | 0214987 | 2/2002 |
| WO | 2005076964 A2 | 8/2005 |
| WO | 2007015067 A2 | 2/2007 |
| WO | 2007040449 A1 | 4/2007 |
| WO | 2008047039 A1 | 4/2008 |

OTHER PUBLICATIONS

Office Action dated Jul. 15, 2013 for U.S. Appl. No. 13/554,710, 37 pages.
International Search Report and Written Opinion dated Oct. 27, 2009 for PCT Application Serial No. PCT/US2009/043861, 14 Pages.
International Search Report and Written Opinion mailed Feb. 23, 2010, for PCT Application No. PCT/US2009/043846, 13 pages.
OA dated Dec. 31, 2009 for U.S. Appl. No. 11/457,129, 16 pages.
OA dated Apr. 17, 2009 for U.S. Appl. No. 11/276,269, 15 pages.
OA dated Nov. 4, 2008 for U.S. Appl. No. 11/276,269, 15 pages.
OA dated Jun. 17, 2010 for U.S. Appl. No. 11/457,129, 15 pages.
Kaul, "Verizon's $250 femto box—A deliberate ploy behind the aggressive pricing?" Posted Tue, Jan. 20, 2009 13:19:46 EST; http://www.abiresearch.com/research_blog/569; © 2009 Allied Business Intelligence, Inc.
OA dated Mar. 29, 2011 for U.S. Appl. No. 12/276,002, 37 pages.
OA dated Apr. 13, 2011 for U.S. Appl. No. 12/276,058, 40 pages.
OA dated Apr. 19, 2011 for U.S. Appl. No. 12/276,238, 22 pages.
OA dated May 5, 2011 for U.S. Appl. No. 12/275,015, 32 pages.
OA dated Jun. 14, 2011 for U.S. Appl. No. 12/275,878, 35 pages.
OA dated Jun. 22, 2011 for U.S. Appl. No. 12/484,072, 38 pages.
OA dated Jul. 7, 2011 for U.S. Appl. No. 12/276,257, 24 pages.
OA dated Jun. 28, 2011 for U.S. Appl. No. 12/275,925, 18 pages.
OA dated Jun. 8, 2011 for U.S. Appl. No. 12/484,026, 30 pages.
OA dated Aug. 18, 2011 for U.S. Appl. No. 12/275,416, 39 pages.
OA dated Sep. 14, 2011 for U.S. Appl. No. 12/276,002, 35 pages.
OA dated Oct. 5, 2011 for U.S. Appl. No. 12/276,058, 37 pages.
OA dated Oct. 6, 2011 for U.S. Appl. No. 12/465,483, 50 pages.
OA dated Oct. 4, 2011 for U.S. Appl. No. 12/484,135, 44 pages.
OA dated Jul. 21, 2011 for U.S. Appl. No. 12/175,293, 30 pages.
OA dated Oct. 24, 2011 for U.S. Appl. No. 12/275,925, 14 pages.
OA dated Nov. 30, 2011 for U.S. Appl. No. 12/275,878, 38 pages.
OA dated Dec. 1, 2011 for U.S. Appl. No. 12/275,996, 44 pages.
OA dated Oct. 25, 2011 for U.S. Appl. No. 12/465,580, 39 pages.
OA dated Nov. 8, 2011 for U.S. Appl. No. 12/465,468, 50 pages.
OA dated Jan. 5, 2012 for U.S. Appl. No. 12/465,585, 43 pages.
OA dated Dec. 28, 2011 for U.S. Appl. No. 12/175,293, 38 pages.
OA dated Nov. 21, 2011 for U.S. Appl. No. 12/484,026, 37 pages.
OA dated Dec. 14, 2011 for U.S. Appl. No. 12/484,072, 44 pages.
OA dated Nov. 1, 2011 for U.S. Appl. No. 12/816,087, 33 pages.
OA dated Mar. 5, 2012 for U.S. Appl. No. 12/465,598, 55 pages.
OA dated May 8, 2012 for U.S. Appl. No. 11/457,129, 38 pages.
OA dated Mar. 19, 2012 for U.S. Appl. No. 12/276,120, 68 pages.
OA dated Mar. 30, 2012 for U.S. Appl. No. 12/484,026, 30 pages.
Notice of Allowance dated Apr. 3, 2012 for U.S. Appl. No. 12/275,996, 38 pages.
OA dated Apr. 10, 2012 for U.S. Appl. No. 12/275,416, 32 pages.
OA dated Apr. 10, 2012 for U.S. Appl. No. 12/484,135, 45 pages.
Notice of Allowance dated Apr. 25, 2012 for U.S. Appl. No. 12/465,468, 35 pages.
OA dated Jul. 16, 2012 for U.S. Appl. No. 12/275,878, 37 pages.
OA dated Jul. 10, 2012 for U.S. Appl. No. 12/465,585, 32 pages.
OA dated Apr. 13, 2012 for U.S. Appl. No. 13/316,106, 35 pages.
OA dated Sep. 5, 2012 for U.S. Appl. No. 12/276,120, 49 pages.
OA dated Aug. 16, 2012 for U.S. Appl. No. 12/465,598, 31 pages.
OA dated Sep. 6, 2012 for U.S. Appl. No. 12/579,957, 51 pages.
OA dated Sep. 10, 2012 for U.S. Appl. No. 12/276,002, 54 pages.
OA dated Oct. 2, 2012 for U.S. Appl. No. 12/484,026, 29 pages.
OA dated Oct. 11, 2012 for U.S. Appl. No. 13/487,794, 45 pages.
OA dated Oct. 9, 2012 for U.S. Appl. No. 13/298,924, 51 pages.
OA dated Nov. 1, 2012 for U.S. Appl. No. 12/276,058, 59 pages.
OA dated Nov. 5, 2012 for U.S. Appl. No. 12/484,072, 52 pages.

(56) References Cited

OTHER PUBLICATIONS

OA dated Nov. 20, 2012 for U.S. Appl. No. 12/275,878, 28 pages.
Japanese Office Action mailed Sep. 13, 2012 for Japanese Patent Application No. 2011-509669, 10 pages.
Canadian Office Action mailed Oct. 30, 2012 for Canadian Patent Application No. 2,722,324, 3 pages.
Japanese Office Action mailed Sep. 13, 2012 for Japanese Patent Application No. 2011-509675, 4 pages.
Office Action dated Dec. 3, 2012 for U.S. Appl. No. 12/275,416, 33 pages.
Office Action dated Jan. 17, 2013 for U.S. Appl. No. 13/554,710, 42 pages.
Final OA dated Feb. 15, 2013 for U.S. Appl. No. 12/579,957.
OA dated Feb. 26, 2013 for U.S. Appl. No. 12/276,120, 59 pages.
Chinese Office Action for Chinese Application No. 200980117263.8 dated Feb. 16, 2013, 7 pages.
Chinese Office Action for Chinese Application No. 200980117188.5 dated Jan. 31, 2013, 11 pages.
Final OA dated Mar. 14, 2013 for U.S. Appl. No. 12/484,072, 34 pages.
Office Action dated Apr. 23, 2013 for U.S. Appl. No. 12/175,293, 41 pages.
Office Action dated Dec. 12, 2013 for U.S. Appl. No. 12/276,120, 78 pages.
Office Action dated Aug. 13, 2013 for U.S. Appl. No. 12/276,120, 66 pages.
Office Action dated Aug. 12, 2013 for U.S. Appl. No. 12/275,416, 36 pages.
Office Action dated Sep. 9, 2013 for U.S. Appl. No. 12/465,585, 45 pages.
Office Action dated Oct. 2, 2013 for U.S. Appl. No. 12/275,878, 38 pages.
Office Action dated Oct. 22, 2013 for U.S. Appl. No. 13/898,910, 50 pages.
Office Action dated Oct. 3, 2013 for U.S. Appl. No. 13/934,644, 17 pages.
Chinese Office Action dated Oct. 24, 2013 for Chinese Patent Application No. 200980117263.8, 13 pages.
Chinese Office Action dated Oct. 21, 2013 for Chinese Patent Application No. 200980117188.5, 11 pages.
Japanese Office Action dated Oct. 3, 2013 for Japanese Patent Application No. 2011-509669, 15 pages.
Notice of Allowance dated Feb. 13, 2014 for U.S. Appl. No. 12/275,878, 34 pages.
Hasan, Mohammad Masud; Huang, Xiadong; Jue, Jason P.; "Survivable Wireless Access Network Design with Dual-homing Capabilities"; IEEE Global Telecommunications Conference, Nov. 27-Dec. 1, 2006, 5 pgs.
Japanese Office Action dated Jan. 16, 2014 for Japanese Patent Application No. 2013-026198, 8 pages.
Office Action dated Mar. 26, 2014 for U.S. Appl. No. 12/465,585, 44 pages.
Office Action dated Mar. 24, 2014 for U.S. Appl. No. 13/934,644, 50 pages.
Notice of Allowance dated Apr. 4, 2014 for U.S. Appl. No. 14/090,802, 63 pages.
Office Action dated Mar. 24, 2014 for U.S. Appl. No. 13/671,191, 63 pages.

* cited by examiner

LOCATION-BASED SERVICES IN A FEMTOCELL NETWORK

CROSS-REFERENCE TO RELATED APPLICATIONS

The subject application is a continuation of U.S. patent application Ser. No. 13/487,794, entitled "LOCATION-BASED SERVICES IN A FEMTOCELL NETWORK," and filed on Jun. 4, 2012, which is a continuation of U.S. Pat. No. 8,219,094, entitled "LOCATION-BASED SERVICES IN A FEMTOCELL NETWORK," and issued on Jul. 10, 2012, which claims priority to U.S. Provisional Patent Application No. 61/052,813, entitled "MANAGEMENT OF ACCESS TO FEMTO CELL COVERAGE," and filed on May 13, 2008. The entireties of each of these applications are incorporated herein by reference.

TECHNICAL FIELD

The subject innovation relates to wireless communications and, more particularly, to location-based services enabled by a femtocell network that serves a confined area.

BACKGROUND

Femtocells—building-based wireless access points interfaced with a wired broadband network—are generally deployed to improve indoor wireless coverage and to offload a mobility radio access network (RAN) operated by a wireless network and service provider. Femtocells typically operate in licensed portions of the electromagnetic spectrum, and generally offer plug-and-play installation. Improved indoor coverage includes stronger signal and improved reception (e.g., voice or data), ease of session or call initiation and session or call retention as well. Offloading a RAN can reduce operational and transport costs for a service provider since a lesser number of end users utilizes over-the-air (OTA) radio resources (e.g., radio frequency bands and channels), which are typically limited.

Coverage of a femtocell, or femto access point (AP), is generally intended to be confined within the bounds of an indoor compound (e.g., a residential or commercial building) in order to mitigate interference among mobile stations covered by a macrocell and terminals covered by the femto AP. Additionally, confined coverage can reduce cross-talk among terminals serviced by disparate, neighboring femtocells as well. Indoor wireless coverage improvements through femtocell also can mitigate customer attrition as long as a favorable subscriber perception regarding voice coverage and other data services with substantive delay sensitivity, or otherwise, is attained. In addition, a richer variety of wireless voice and data services can be offered to customers through a femtocell since such service offerings do not rely primarily on mobility RAN resources.

As deployment of femtocells increase, backhaul resources demand increases with ensuing increase in procurement, deployment, and maintenance cost of such resources. In addition, increase in density of femtocell deployments, traffic and signaling exchanged between a network management component, such as a radio network controller or a femtocell gateway, and a femto AP also increase. Related costs associated with operation of femtocell network in heavy-traffic conditions increase as network management components and management thereof become more complex in order to efficiently exchange traffic and control with deployed femto APs. Heavy-traffic conditions can cause congestion in the backhaul network and delays during communication, which can lead to diminished perceived quality of service and related subscriber attrition. Moreover, costly infrastructure and heavy-traffic operation conditions can curtail provision of value-added services that can provide commercial differentiator or advantages to a wireless service provide that deploys and manages a femtocell network. Mitigation of escalation of costs and reduction in operation and management complexity can avoid a trade-off with advantages provided by femtocells and associated subscriber attrition.

DETAILED DESCRIPTION

Figure 1:
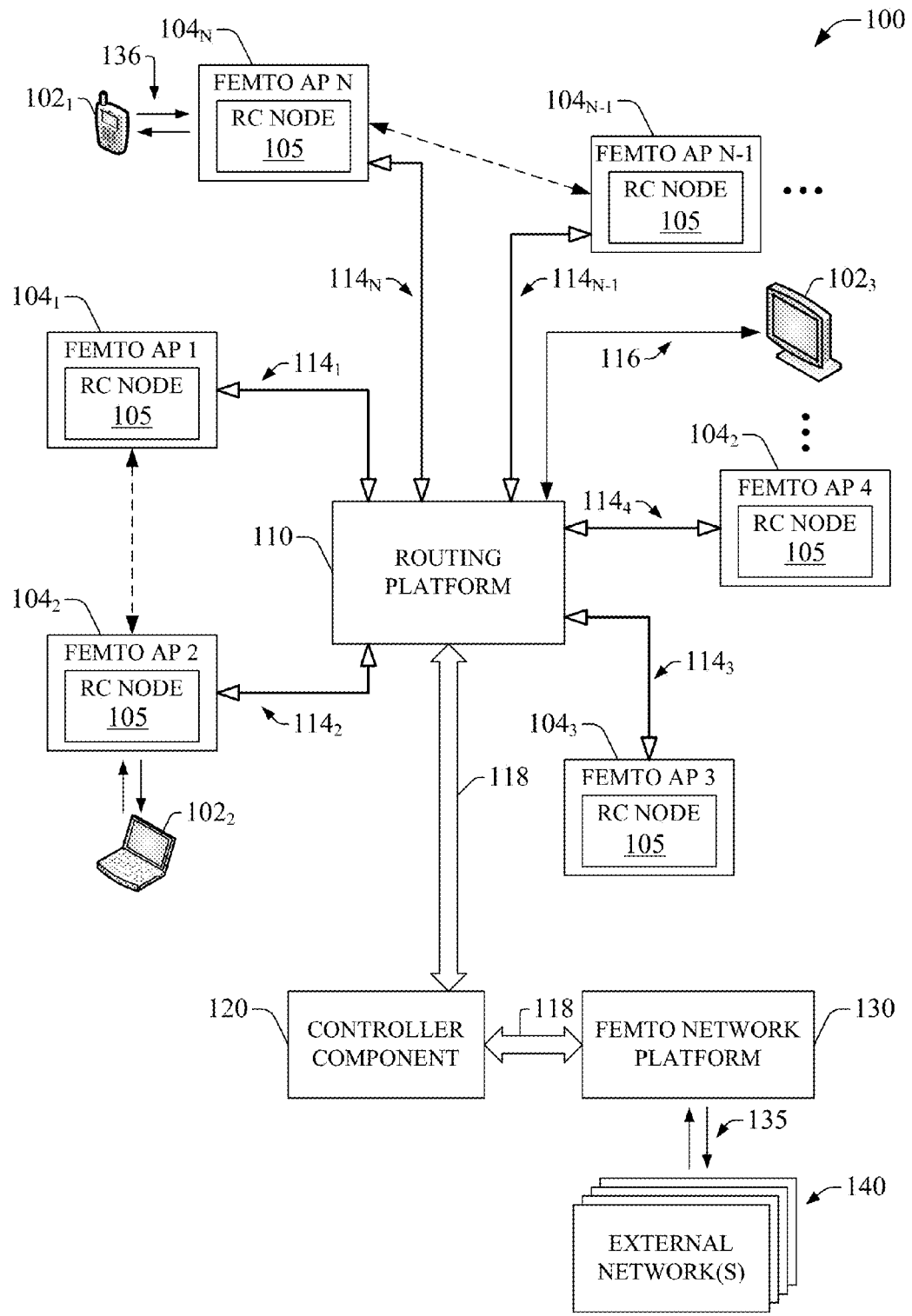
FIG. 1 illustrates a diagram of an example enterprise femto network in accordance with aspects of the subject specification.

The subject innovation is now described with reference to the drawings, wherein like reference numerals are used to refer to like elements throughout. In the following description, for purposes of explanation, numerous specific details are set forth in order to provide a thorough understanding of the present innovation. It may be evident, however, that the subject invention may be practiced without these specific details. In other instances, well-known structures and devices are shown in block diagram form in order to facilitate describing the present invention. The subject application is related to co-pending U.S. patent application Ser. No. 12/465,585, entitled "COMMERCE AND SERVICES IN A FEMTO-CELL NETWORK," and filed on May 13, 2009, co-pending U.S. patent application Ser. No. 12/465,580, entitled "INTRA-PREMISES CONTENT AND EQUIPMENT MANAGEMENT IN A FEMTOCELL NETWORK," filed on May 13, 2009, and co-pending U.S. patent application Ser. No. 12/465,468, entitled "FEMTOCELL ARCHITECTURE FOR INFORMATION MANAGEMENT," and filed on May 13, 2009. The entireties of each of these applications are incorporated herein by reference.

As used in this application, the terms "component," "system," "architecture," "platform," "node," "layer," "selector," "interface," "module," and the like are intended to refer to a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, a program, and/or a computer. By way of non-limiting illustration, both an application running on a server and the server can be a component. One or more components may reside within a process and/or thread of execution and a component may be localized on one computer and/or distributed between two or more computers. These components also can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry that is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can include a processor therein to execute software or firmware that confers at least in part the functionality of the electronic components. An interface can include input/output (I/O) components as well as associated processor, application, and/or API components.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Moreover, terms like "user equipment," "mobile station," "mobile," "mobile device," "subscriber station," "subscriber equipment," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "base station," "Node B," "evolved Node B (eNode B)," home Node B (HNB)," "home access point (HAP)," or the like, are utilized interchangeably in the subject specification and drawings, and refer to a wireless network component or apparatus that serves and receives data, control, voice, video, sound, gaming, or substantially any data-stream or signaling-stream from a set of subscriber stations. It is noted that in the subject specification and drawings, context or explicit distinction provides differentiation with respect to access points or base stations that serve and receive data from a mobile device in an outdoor environment, and access points or base stations that operate in a confined, primarily indoor environment. Data and signaling streams can be packetized or frame-based flows.

Furthermore, the terms "user," "subscriber," "customer," "consumer," "prosumer," "agent," "owner" and the like are employed interchangeably throughout the subject specification, unless context warrants particular distinction(s) among the terms. It should be appreciated that such terms can refer to human entities or automated components supported through artificial intelligence (e.g., a capacity to make inference based on complex mathematical formalisms) which can provide simulated vision, sound recognition and so forth. As utilized herein, the term "prosumer" indicate the following contractions: professional-consumer and producer-consumer.

Further yet, the terms "wireless network" and "network" are used interchangeable in the subject application, when context wherein the term is utilized warrants distinction for clarity purposes such distinction is made explicit. Likewise, the terms "femtocell access point", "femto access point", "femtocell," "femto" and the like also are utilized interchangeably.

The subject innovation provides system(s) and method(s) to route traffic and signaling between a set of networked femto access points (APs) and enable location-based services. A femto AP in the set of femto APs is functionally linked to a routing platform that manages traffic and signaling, and is functionally connected to a controller component that relays at least part of data and control to a femto network platform. The femto network platform allows access to one or more external networks. Routing platform assesses billing charges associated with a call session served at least in part through one or more femto APs in the set of femto APs and the routing platform. Call sessions can include intra-network or inter-network communication, wherein intra-network communication can include push-to-point delivery of traffic and signaling, while inter-network communication can include exchange of data and control among a device served through an external network and a device served through a femto AP linked to the routing platform. In addition, routing platform can effect soft handover of call sessions amongst two femto APs in the set of femto APs, and it can implement hard handover of a call session between a femto AP and a component in an external network that can serve the call session.

Routing platform can exchange signaling with one or more femto APs to enable, at least in part, location-based services based at least in part on identifier(s) for a femto AP, access privileges, or time-of-flight measurements that assess propagation timing between a mobile device and a femto AP. In another aspect, routing platform can supply timing configuration and drive time-of-flight measurements to triangulate a position of an apparatus with wireless capability located within coverage area spanned through the set of femto APs. The timing configuration can enable a predetermined spatial resolution of location estimates. Location estimates can be recorded and conveyed to a consumer layer.

Aspects, features, or advantages of the subject innovation can be exploited in substantially any wireless telecommunication, or radio, technology; for example, Wi-Fi, Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP UMTS; High Speed Packet Access (HSPA); High Speed Downlink Packet Access (HSDPA); High Speed Uplink Packet Access (HSUPA), or LTE Advanced. Additionally, substantially all aspects of the subject innovation can include legacy telecommunication technologies.

It is noted that various aspects, features, or advantages of the subject innovation are illustrated in connection with femto access point(s) and associated femto network platform, such aspects or features also can be exploited in indoor-based base stations (e.g., home-based access point(s), enterprise-based access point(s)) that provide wireless coverage through substantially any, or any, disparate telecommunication technologies such as for example Wi-Fi (wireless fidelity) or picocell telecommunication.

FIG. 1 illustrates a diagram of an example enterprise femto network architecture 100 in accordance with aspects of the subject specification. A set of femto access points 104₁-104ₙ, with N a natural number, can be functionally connected to a routing platform 110 that can be functionally coupled to a controller component 120, which can be operationally linked to a femto network platform 130. It should be appreciated that a single backhaul pipe 118 operationally connects routing platform 110 and controller component 120. Likewise, a single backhaul pipe 118 connects controller component 120 and femto network platform 130. In an aspect, femto network platform 130 can be functionally coupled, via one or more reference link(s) 135, to external network(s) 140 which can include service network(s) such as an internet protocol (IP) multimedia subsystem (IMS). In another aspect, in 3GPP UMTS radio technology, controller component 120 can be embodied in a radio network controller. It is noted that in one or more alternative or additional embodiments, controller component 120 can reside within femto network platform 130 or within one of external network(s) 140, in such an embodiment, femto network platform 140 can connect to routing platform 110 via the one external network among external network(s) 140. It should further be appreciated that example enterprise femto network architecture 100 enables femto APs 104₁-104ₙ to be mutually connected, via routing platform 110, in a mesh network configuration, also termed herein as a mesh femto network. The portion of the enterprise femto network within the coverage area spanned by femto APs 104₁-104ₙ is private as opposed to public such as a macrocell network.

The number of femto APs 104_λ, with $\lambda = 1, 2 \ldots N$, connected to the routing platform 110 can be based at least in part on at least one of a number of ports on or bandwidth available to routing platform 110. Femto APs 114_λ are functionally connected to routing platform 110 through links 114_λ, which can be broadband, backhaul wired links (e.g., optical fiber backbone, twisted-pair line, T1/E1 phone line, a digital subscriber line (DSL) either synchronous or asynchronous, an asymmetric ADSL, or a coaxial cable . . . ) or a wireless (line-of-sight (LOS) or non-LOS) links. Backhaul link(s) 118 also can wired or wireless. In an aspect, in 3GPP UMTS radio technology, a link 114_λ can be embodied in at least one of an Iur interface or an Iuh interface. It is noted that the number of channel elements of a link 114_λ can be lower that the number of channel elements in backhaul link 118. Thus, the plurality of femto APs 104₁-104ₙ can be served via femto network platform 130, through single backhaul pipes 118, with less backhaul resources than in a conventional system in which a backhaul pipe 118 is functionally connected to each femto AP.

Femto APs 104₁-104ₙ are deployed within a confined coverage area which can include either a single-floor or multi-floor facility or enterprise. Deployment plan generally minimizes dead spots and includes a number of femto APs sufficient to achieve operational redundancy, such that if one or more of the provisioned femto APs fails, disparate additional femto AP(s) functionally connected to routing platform 110 can be employed for communication. Thus, the mesh femto network can be self-healing. An enterprise can include, but is not limited to including, one of an office building; a residential complex, a business building such as department store, a bank, a restaurant, or a warehouse; a government facility; a school; a hospital; a hotel; a factory; an airport; a recreation or city park; or the like.

Figure 2A:
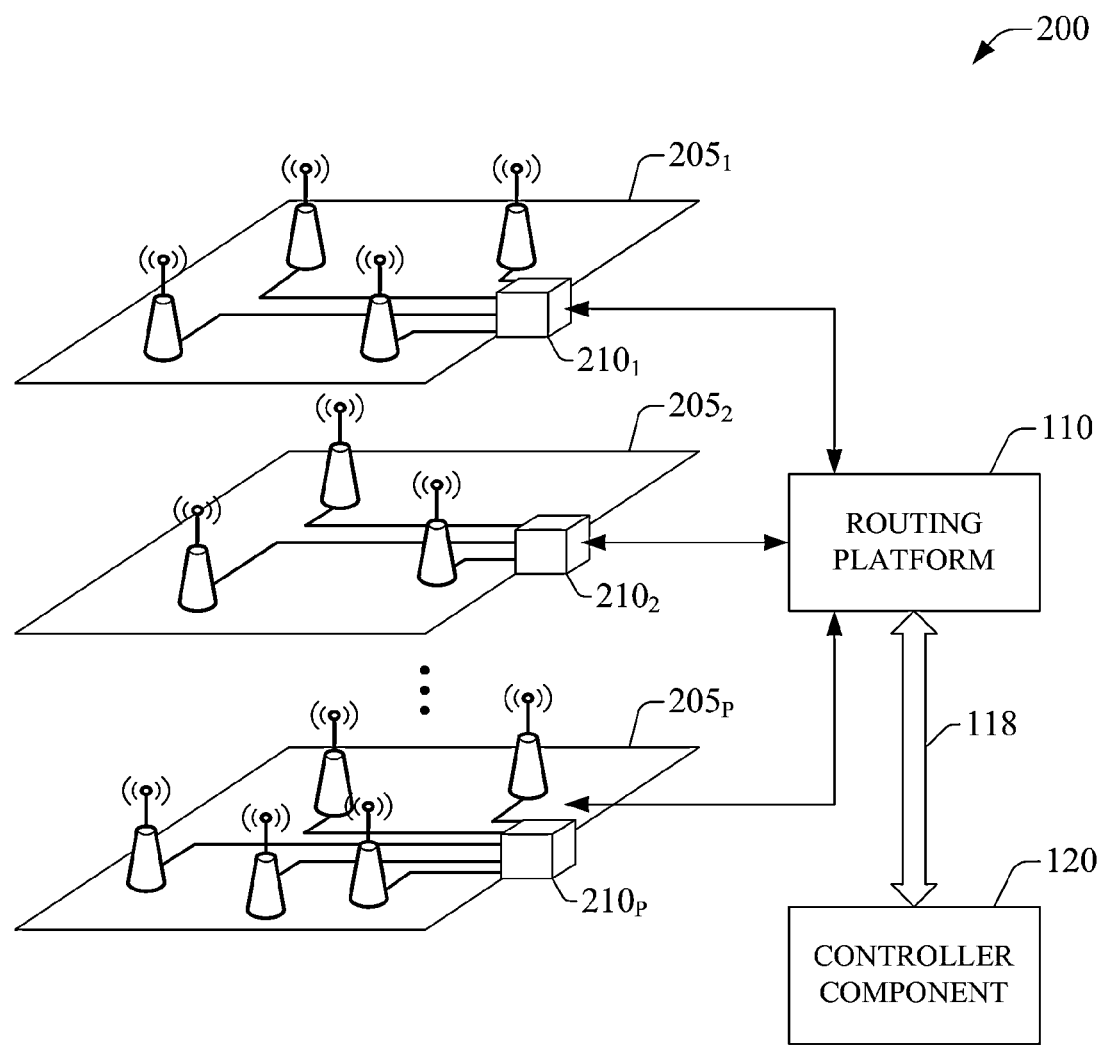
FIGS. 2A-2C illustrate, respectively, a block diagram of an example multi-coverage-area femto mesh network, a block diagram of an example femto mesh network in which routing in a multi-loci environment is decentralized, and an example femto mesh network wherein various routing platforms related to various enterprise deployments are multiplexed in accordance with aspects described herein.

As an illustration of multi-floor networked embodiments, FIG. 2A displays a block diagram of an example multi-coverage-area femto mesh network 200 in accordance with aspects described herein. Coverage areas, 205_μ ($\mu = 1, 2 \ldots P$) can include indoor environments such as floors in a building and, at least partially, outdoor environments such as parking lots; terraces, decks, or verandas; or sports fields or courts. In each coverage area 205_μ, a network interface device (NID) 210_μ centralizes broadband link(s), illustrated as thick lines without arrowheads (for clarity), from each deployed femto AP. NIDs 210_μ are functionally connected to routing platform 110. Deployed femto APs can be further connected to a single backhaul pipe 116 through routing platform 220. Routing platform 220 can direct traffic among wireless devices located in disparate coverage areas. It is noted that routing functionality provided by routing platform 220 is centralized. As an example, consider a scenario in which the example enterprise femto network architecture 200 is deployed in a multi-floor building wherein multiple femto APs can be deployed on each floor, e.g., coverage area $205_\mu$, of the building. In this example, a mobile device on a first floor, e.g., $205_2$, connected to a femto AP on the first floor can establish communication (e.g., voice or data) with another mobile device on a second floor, e.g., 205P, connected to a femto AP therein, without accessing a femto network platform linked to controller component 120.

Figure 2B:
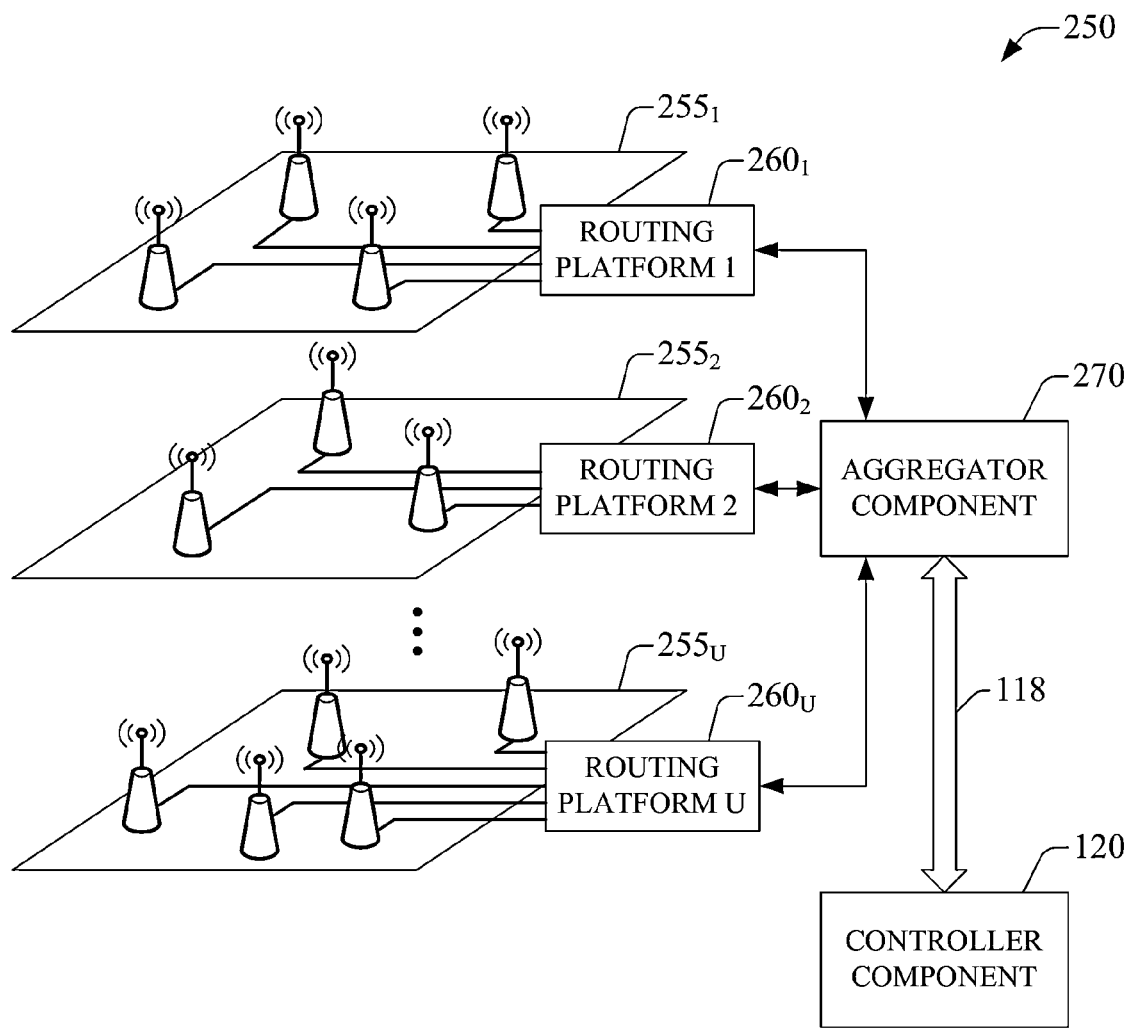

Alternatively or additionally, FIG. 2B displays a block diagram of an example femto mesh network 250 in which routing in a multi-coverage-area environment is decentralized, effected by a set of routing platforms $260_1$-$260_U$, U is a natural number, and each coverage area $255_\gamma$, with $\gamma=1, 2 \ldots$ U, linked to each routing platform in the set. An aggregator component 260 interfaces the multi-area femto enterprise network architecture 250 with controller component 120. The multiple routing platforms $260_\gamma$ can communicate with each other such that configuration information with respect to femto APs associated with each routing platform and devices operationally connected to the femto APs is available to each routing platform $260_\gamma$; configuration information can enable, at least in part, internal routing of traffic. An aggregator component 270 can operate as at least one of a pass-through element or as a traffic shaping component, preserving QoS in accordance with predetermined QoS profile(s) for various types of traffic or signaling. As illustrated, one routing platform $260_\gamma$ is deployed on each coverage area $220_\gamma$, with $\gamma=1, 2 \ldots$ U, wherein each coverage area can be a floor of a building (e.g., an office building, a school, a department store) and routing platforms $260_\gamma$ on each floor can be mutually functionally connected to create an enterprise femto mesh network structure that can cover the entire building. It is noted that based at least in part on the size of a coverage area $255_\gamma$, more than a single routing platform can be deployed in the coverage area $255_\gamma$. Multiple femto APs can be functionally connected to a single routing platform $260_\gamma$, and multiple routing platforms $220_1$-$220_u$ can be connected together to create a larger mesh femto network.

Processor(s) (not shown) can provide at least part of the functionality of aggregator component 260. To operate or confer at least in part functionality to the aggregator component 260, the processor(s) can store information in, and retrieve information from, a memory (not shown). The information can include at least one of code instructions, data structures, program modules, or the like.

Figure 2C:
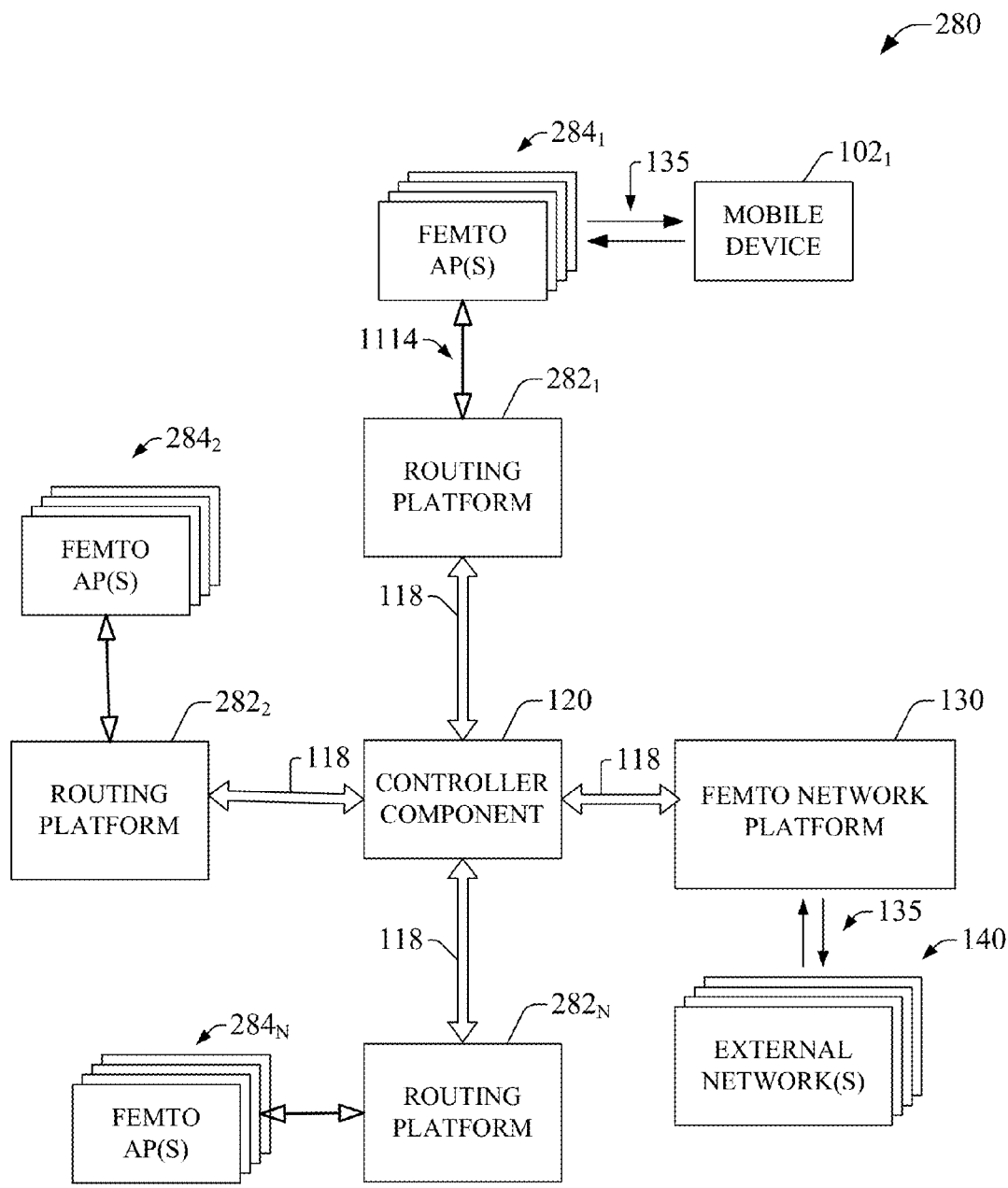

Further, FIG. 2C illustrates an example femto mesh network 280 wherein various routing platforms related to various enterprise deployments can be multiplexed by employing a single controller component 120. According to an aspect, controller component 120 can receive information from a set of routing platforms, $282_1$-$282_N$, wherein N is a natural number. Each of the routing platforms $282_1$-$282_N$ can be connected to respective sets of multiple femto APs $284_1$-$284_N$, which facilitate connectivity to/from mobile device $102_1$ connected, e.g., to a respective set of femto APs $284_1$. Each routing platform $282_1$-$282_N$ can receive data from a mobile device attached to a set of femto APs $284_1$-$284_N$ within the enterprise femto architecture or network. Moreover, routing platforms $282_1$-$282_N$ can perform an analysis to determine information associated with routing of the received data (e.g. source address, destination address, etc.). Further, a route can be determined for transferring the packet from the routing platform based in part on the analysis and/or user defined rules or policies and/or user preferences. In particular, routing platforms $282_1$-$282_N$ can determine whether a soft-(indicated with dashed lines in FIG. 1) or hard-handover can be performed. When a hard handover is to be performed, routing platforms $282_1$-$282_N$ can route the data to the femto network platform 130 controller component 120. It is noted that controller component 120 can typically include functionality of a second RNC or most any other network management component associated with the femto network platform 130, which can be embodied at least in part in a FGW. It is noted, however, that in the subject innovation controller component 120 does not effect any RNC function(s) or operation(s). In an aspect, as illustrated in example mesh femto network 280, controller component 130 can multiplex the set of routing platforms $282_1$-$282_N$ related to various enterprise deployments.

Figure 3:
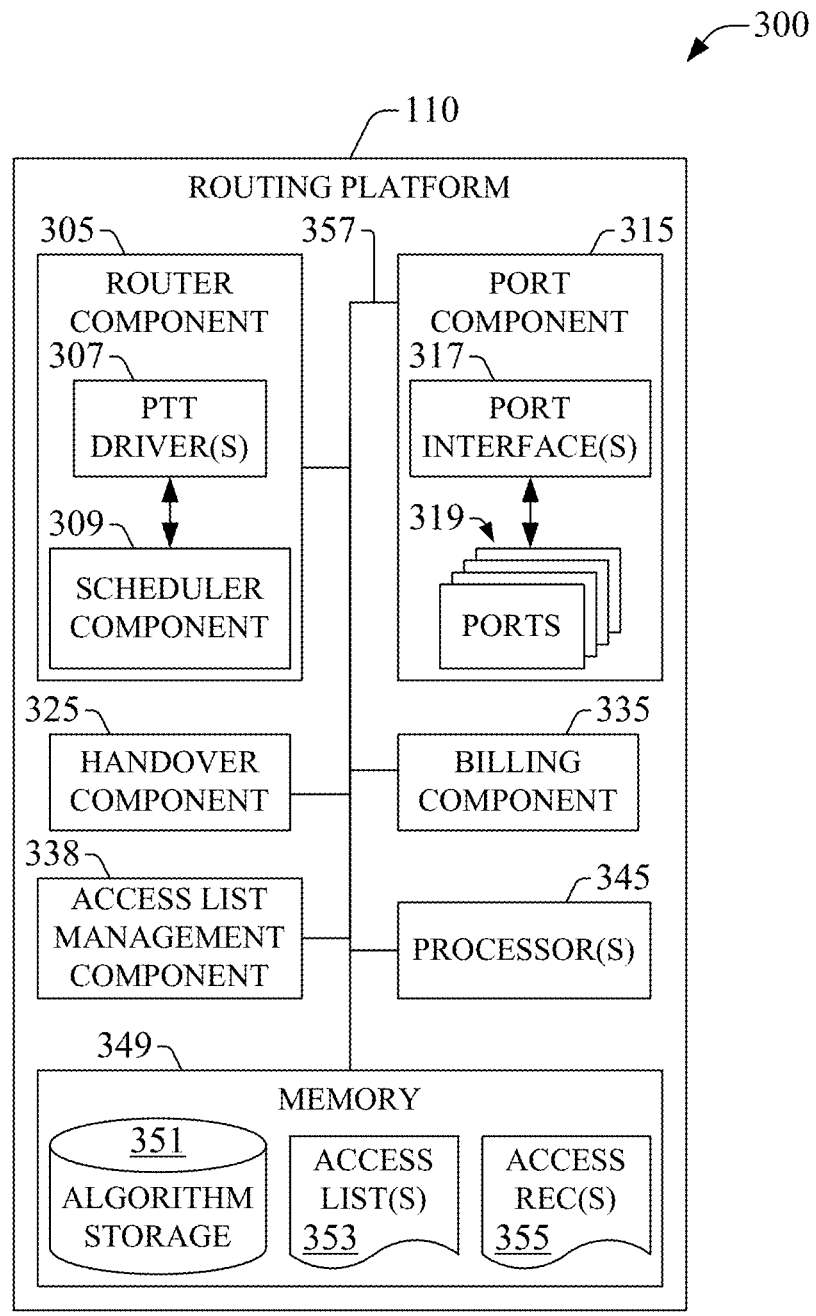
FIG. 3 displays a block diagram of an example embodiment of a routing platform that is part of an enterprise femto network architecture in accordance with aspects disclosed herein.

Connections amongst backhaul links $114_\lambda$ and routing platform 110, NIDs $210_\mu$ and routing platform 110, and routing platform 110 and aggregator component 270 can be effected through a port component 315 within routing platform 110, as illustrated in example embodiment 300 shown in FIG. 3. Port component 315 can include port interface(s) 317 to configure one or more of ports 319, which can include parallel ports (e.g., GPIB, IEEE-1284), serial ports (e.g., RS-232, V.11, USB, FireWire or IEEE-1394 . . . ), Ethernet ports, V.35 ports, X.21 ports, or dry contacts, or the like. Port interface(s) 317 can include a wireless interface such as a wireless card and associated circuitry to implement telecommunication. In addition, port interface(s) 319 can include one or more physical docks that support physical connectors for respective ports 319. Routing platform 110 can be configured, or programmed, to communicate wirelessly with one or more femto AP $104_\lambda$ rather than through routing cables. Configuration can be accomplished trough a display interface (not shown) that enables data entry in routing platform 110, or through a device such as a computer, mobile or otherwise, connected to port component 315.

As illustrated in FIG. 1, each femto AP $104_\lambda$, or femto APs illustrated in embodiments 200 and 250, that is connected to routing platform 110 can include a radio controller (RC) node 105 that includes at least part of the functionality of a radio network controller. Routing platform 110 can functionally connect RC nodes 105 between two or more femto APs deployed within example femto enterprise network system 100. As indicated supra, link(s) $114_\lambda$ can include at least an Iur interface that can route packet stream(s) between the functionally connected two or more femto APs. An RC node 105 can have substantially the same functionality as that controller component 120. However, in one or more architecture(s) or embodiment(s), RC node 105 can have less complexity than controller component 120. Having an RC node 105 in each femto AP $104_\lambda$ can result in an optimal (e.g., sub-linear) or nearly optimal (e.g., linear) scaling of processing demand at routing component with respect to the number of provisioned femto APs in the femto enterprise network architecture. Processing demand in the femto enterprise network increases due to increased routing or scheduling processing. It is noted that scheduling relates to scheduling of packet delivery rather than scheduling of radio resources, which is implemented by routing platform 110. When a femto AP is added to the femto mesh network 100, the RC node 105 associated with the femto AP can provide RNC functionality thereto and thus the mesh network. However, demand for backhaul resources, e.g., backhaul link 118, and controller component 120 does not grow with an increase in the number of femto APs functionally connected to routing component 110. Accordingly, built-in RNC functionality can improve scalability with respect to a networked configuration in which routing platform also acts as a radio network controller.

Routing platform 110 can enable user plane connections directly, and can establish communication, e.g., exchange of voice or data and signaling, between two or more femto APs, e.g., femto AP $104_2$ and $104_N$. Moreover, routing platform 110 can enable communication between mobile devices, e.g., $102_1$ and $102_2$, attached to disparate femto APs, wherein traffic and signaling associated with the communication is routed within the example femto enterprise network 100 without delivery of data or management packets to femto network platform 130. For example, routing platform 110 can direct traffic generated by mobile device $102_1$ served through femto AP $104_N$ to wireless device $102_2$ served by femto AP $104_4$. Communication amongst mobile device $102_1$ and wireless device $102_2$ can be push-to-talk communication. Alternatively or additionally, routing platform 110 can allow push-to-talk communication between a mobile device and a pseudo-stationary tethered device such as $102_3$. It is noted that, in an aspect, routing platform 110 is traffic agnostic in that a first device, mobile or otherwise, can operate in a first radio technology disparate from a second radio technology employed by a second device, mobile or otherwise, that communicates with the first device through routing platform 110 and via respective femto APs. In an example embodiment 300, illustrated in FIG. 3, routing component 110 can include push-to-talk driver(s) 307 to enable at least in part point-to-point communication among one or more devices, mobile or otherwise in the femto mesh network 100. In view of such internal communication, for outgoing communication(s) off the example mesh femto network 100, routing platform 110 can allocate bandwidth primarily for control, or signaling, and thus traffic on the backhaul network can be substantially reduced. In addition, such communication internal to example enterprise femto network system 100 can reduce communication delay, with ensuing improvement of perceived QoS for latency-sensitive content such as multiplayer gaming.

In an aspect, routing platform 110, via router component 305, can receive carrier-frequency information associated with channels employed for telecommunication within the coverage area of an enterprise femto network 100. Router component 305 can aggregate carrier-frequency data to form a carrier-frequency map. In an aspect, the carrier-frequency map can enable load balancing of traffic within the enterprise femto network 100 through dynamic allocation of bandwidth to specific femto APs functionally connected to the routing platform. Scheduler component 309 can signal a bandwidth allocation to a femto AP within the enterprise femto network 100.

Routing platform 110 can direct a packet received from a femto AP, e.g., $104_{N-1}$, based in part on routing information. In an aspect, routing platform 110 can receive a communication packet from one of the multiple femto APs $104_1$-$104_N$ and can determine routing information associated with the communication packet. In an aspect, the routing information can indicate that the communication packet is to be transferred to femto network platform 130. Accordingly, routing platform 110 can perform a hard handover and direct the packet to femto network platform 110 through controller component 120. In another aspect, the routing information can indicate that the packet can be transferred internally from a first femto AP, e.g., $104_N$, to a second femto AP, e.g., $104_2$, functionally connected to routing platform 110. Moreover, in such case, routing platform 110 can perform a soft handover between a first femto AP ($104_2$) and a second femto AP (e.g., $104_3$) and establish communication such that dead spots or issue scenarios can be avoided or mitigated. Furthermore, routing platform 110 can determine control information, or signaling, for traffic routed directly between femto APs and route the control information, or signaling, to femto network platform via controller component 120 through backhaul pipe 118.

In an example embodiment 300, routing platform 110 includes a router component 305 that can direct traffic and signaling among a set of deployed femto APs, e.g., femto APs $104_1$-$104_N$. Traffic can be routed in accordance at least in part with a set of one or more algorithm(s) retained in memory element 349. Router component 305 can determine a near-optimal or optimal route for a received data or management packet, to avoid network congestion within mesh femto network 100. In addition, router component 305 also can configure point-to-point communication as part of routing functions based at least in part on channel conditions. Moreover, router component 305 can utilize configured access list(s) 353 to route traffic and signaling and ensure data integrity or self-healing routing.

Access list(s) 353 can regulate, at least in part, a level of service provided to user equipment through a femto AP, e.g., $104_{N-1}$. Access list(s) can comprise at least one of whitelist(s) that at least in part identify a set of devices that can be provided wireless service through a femto AP, or blacklist(s) that can explicitly exclude one or more wireless devices from femto service. In addition, wireless devices in blacklist(s) can prompt exception handling procedures that include issuance of alarm(s), notification to authorities, tracking of device location within the enterprise femto network 100, or the like. In an aspect, access list(s) 353 can be received from femto network platform 130, in which access list(s) 353 can resided within a subscriber database and can be configured through at least one of external network(s) 140. In another aspect, routing platform 110 can include access list management component 338 which can generate or modify, at least in part, access list(s) 353 (e.g., whitelist(s) or blacklist(s)) based at least in part on signaling received from one or more femto APs within the set of femto APs deployed as part of the femto enterprise network 100. Access list(s) 353 generated through access list management component 338 can be active for a predetermined period, and after such period elapses can be deleted, either logically or physically, based at least in part on signaling received from one or more network components. Signaling can include mobile device identifier attribute(s). Access list management component 338 can either accept or reject such attribute(s) based at least in part on a set of criteria (not shown) which can be retained within memory 349. Further, for accepted mobile device identifier attribute(s), a default or initial level of access; for instance, almost all or all femto APs deployed as part of enterprise femto network 100 can provide service to an identified mobile device. Default or initial level of access can be modified subsequently based at least in part on additional signaling received by routing platform 110. As an illustration, the set of acceptance or rejection criteria can include at least one of the following. (i) Valid mobile device identifier, e.g., wireless device numbers such as IMSIs, MSISDNs, or other codes or tokens. (ii) Active mobile device identifier or identifier flagged for update; e.g., an identifier that corresponds to an old phone number that is to be updated to a current number. (iii) Status of election (e.g., opt in) or non-election (e.g., opt out) flags for inclusion in a whitelist, wherein status is conveyed, for example, via a K-bit word (K is a natural number) within an entry for the mobile device in a subscriber database. (iv) Operational capabilities of the identified mobile device (e.g., wireless technology utilized by the device such as second generation (2G), third generation (3G), or fourth generation (4G) technologies, radio frequency bands in which the mobile device can receive communications . . . ). (v) Commercial standing of the identified mobile device; e.g., good standing or outstanding bill payments, hotlined mobile device in view of recurring lack of timely payments for service, stolen device . . . ; or the like.

Furthermore, router component 305 can include a scheduler component 309 to establish quality of service (QoS) for communication among two or more devices in accordance at least in part with at least one of traffic priority profile or QoS class (e.g., best effort, maximum bit-error-rate (BER), guaranteed data rate). In an aspect, during provisioning of a femto AP, which can be effected by a provisioning server within femto network platform 130, scheduler component 309 can determine or configure at least one of quality of service (QoS) or one or more queuing functions that can facilitate management of content(s), e.g., traffic or signaling. Scheduler component 309 also can employ load-balancing techniques, which can be implemented through algorithms retained in algorithm storage 351, to enable efficient network or resource(s) utilization.

In addition, scheduler component 309 can utilize access list(s) 347 that control access to one or more femto APs by one or more mobile device to route traffic, e.g., a data packet, and signaling, e.g., a management packet, amongst femto APs in the enterprise femto architecture. In an aspect, access list(s) 347 can allow access to a femto AP, e.g., the access list is a white list, or can include black list(s), which can explicitly determine mobile devices that are denied access to service through one or more femto APs and trigger an exception handling subsequent to attachment attempt(s) effected by black listed mobile devices. In an aspect, exception handling can include authorization of attachment to a femto AP and notification of an authority, as discussed below.

To perform almost any or any handover (e.g., soft handover) internal to example mesh femto network 100 without accessing femto network platform 130, e.g., delivering signaling or traffic thereto, routing platform 110 also can configure and exploit user-plane connection(s). In an aspect, routing component 110 can exploit links $114_\lambda$, e.g., Iur interfaces, between femto APs $104_\lambda$ to enable soft handover. As illustrated in example embodiment 300, routing platform 110 can include a handover component 325 to administer handoff of a wireless device served by a first femto AP to a second femto AP in the femto enterprise network architecture 100. Handover component 325 can implement hard handoff or soft handoff in accordance at least in part with a set of handover criteria (not shown), which can be configurable by a wireless service provider on an event basis or as a function of time. In an aspect, soft handover can be effected at least in part based on at least one or more RF boundaries, which can be configured through a timing component, as discussed below. In example embodiment 300, memory 349 can retain handover criteria (not shown in FIG. 3).

Routing platform 110 also can enable communication of content(s), or traffic, among a device $102_3$ served primarily via a network that is part of external network(s) 140, such as one of a non-mobile broadband internet service network, a broadband digital cable network, or a macrocell network and mobile devices served through a femto AP $104_\lambda$. In an aspect, device $102_3$ can be an IP television (IPTV) tuner that can receive caller identification information when a call directed to a mobile device $102_1$ is received by routing platform 110. Such a feature can advantageous to alert a subscriber in a residence wherein the subscriber is associated with the mobile device 1021 and separated there from while the subscriber utilizes device $102_3$. In another aspect, when the enterprise is a wholesale store, or big-box store, device $102_3$ can be a voice-over-IP (VoIP) transceiver in a customer service platform which routing platform 110 can connect to a mobile device, e.g., $102_2$, served through a femto AP, e.g., $104_2$, within the enterprise femto network system 100 in order to provide customer assistance to a consumer associated with the mobile device. User equipment (UE) that operates within example enterprise femto network system 100 can include almost any or any electronic device that can connect wirelessly to a femto AP or can be linked operationally to a port within routing platform 110. In addition to example UEs provided supra, user equipment can include mobile phones; media players; digital cameras; digital media recorders such as digital video recorders (DVRs); laptop computers; personal digital assistants (PDAs); personal computers; printers; scanners; digital photo frames; navigation device such as a global positioning system (GPS) module; gaming modules; and so forth. Further, it can be appreciated the UEs can be mobile, stationary, or pseudo-stationary, and wireless or tethered.

In an aspect, during internal communication within the enterprise femto architecture 100, routing platform 110 can establish and retain a control link to femto network platform 130, e.g., to gateway node(s) therein, that can be employed by femto network platform 130, via a billing server, to process billing charges; it should be appreciated that billing processing can be effected by an application layer within one of external network(s) 140 such as an IMS network. In example embodiment 300, billing component 335 can allow to establish the control link and convey it to femto network platform 130 to update a billing database associated with a billing server that can apply, for example, different charges for internal communication within the enterprise femto network architecture 100 and external communication with femto network platform 130. Charges associated with internal communication can be lower than charges associated with external communication. The control link also can be retained in a memory, e.g., a buffer, within routing platform 110 such that if a failure occurs in femto network platform 130, internal communication within the mesh femto network 100 can continue uninterruptedly. Retained control data can be transferred to femto network platform 130 for billing purposes when it resumes operation(s).

Example enterprise femto network system 100 also can afford multiple billing schemes associated with a wireless service provider that administers the example femto network architecture 100. In example embodiment 300, billing schemes can be retained in memory 249. In an aspect, the one or more billing schemes can be dictated, at least in part, by access configuration(s) retained in access list(s) 347. In an example billing scheme, the wireless service provider can charge a fixed rate for external communication, for example, when traffic received at the router platform 102 is conveyed to the femto network platform 130 through backhaul link(s) 118, e.g., Iuh interface, whereas internal communication within the example enterprise femto network architecture 100 can be free of charge. It is noted that in such example billing scheme, the wireless service provider can charge a fee directed to operation and maintenance associated with the mesh femto network. In another example billing scheme, the wireless service provider can implement maintenance of the mesh femto network 100 free of charge, but can charge a high rate for external communication with femto network platform 130 and a low rate for internal communication within the mesh femto network. It is to be appreciated that the subject specification is not limited to the aforementioned illustrative billing scheme(s) and most any or any billing scheme can be configured and employed. The wireless service provider can configure or predefine billing charges based at least in part on criteria such as served customer segment, an implemented promotional campaign, marketplace, operational costs, or the like. In example embodiment 300, billing component 335 can configure, at least in part, and implement one or more billing schemes for served traffic within femto enterprise femto network architecture 100 or for traffic delivered to or received from a femto network platform. In addition, billing component 335 can modify such configured billing charges dynamically, e.g., as a function of time, based at least in part on operational conditions such as available network bandwidth, load of one or more deployed femto APs within an enterprise femto network system, volume of traffic manipulated by routing platform 110, or the like.

In an aspect, routing platform 110 can manage different virtual local area network(s) (VLAN(s)) such as one or more of a VLAN for voice or data traffic on user plane; a VLAN for control signaling transported through at least a portion of link(s) 1141, which can be embodied in an Iur interface; a VLAN for control signaling conveyed to femto network platform 130; or the like. In an example, routing platform 110 can enable bandwidth management for the different VLANs.

As illustrated in example embodiment 300, routing platform 110 includes processor(s) 345 configured to confer, and that confers, at least in part, functionality to substantially any or any component within routing platform 110 in accordance with one or more aspects of the subject innovation. Processor(s) 345 is illustrated as external to the various functional elements or components of routing platform 110; however, processor(s) 345 can be distributed amongst such various functional elements or components. Processor(s) 345 is functionally coupled to each functional element or component and to memory 349 through bus 357, which can be embodied in at least one of a memory bus, a system bus, an address bus, or one or more reference link(s) or interface(s). Processor(s) 345 can store information in, and retrieve information from, memory 349 necessary to operate and/or confer at least in part functionality to each of the components that reside within routing platform 110. The information can include at least one of code instructions, data structures, program modules, or the like.

At least an advantage of example femto enterprise architecture 100 is that it reduces at least one of backhaul network traffic or signaling among provisioned femto APs that are part of the femto enterprise network and a femto network platform, which can include controller node 120.

At least another advantage of example femto enterprise architecture 100 is that routing can be self-healing; for instance, traffic can be routed via an alternative femto AP when an intended femto AP is non-functional or radio communication thereby is otherwise impaired. In addition, data and signaling can be cached or recorded for subsequent utilization to mitigate, at least in part, communication disruption.

At least a further advantage of example enterprise femto network architecture 100 is that it can mitigate utilization of private branch exchange (PBX), or internet protocol (IP)-PBX, resources for intra-premises communication, or communication among a mobile device served through a femto wide radio access network, or a wide area network, which can be mobile or otherwise.

Figure 4:
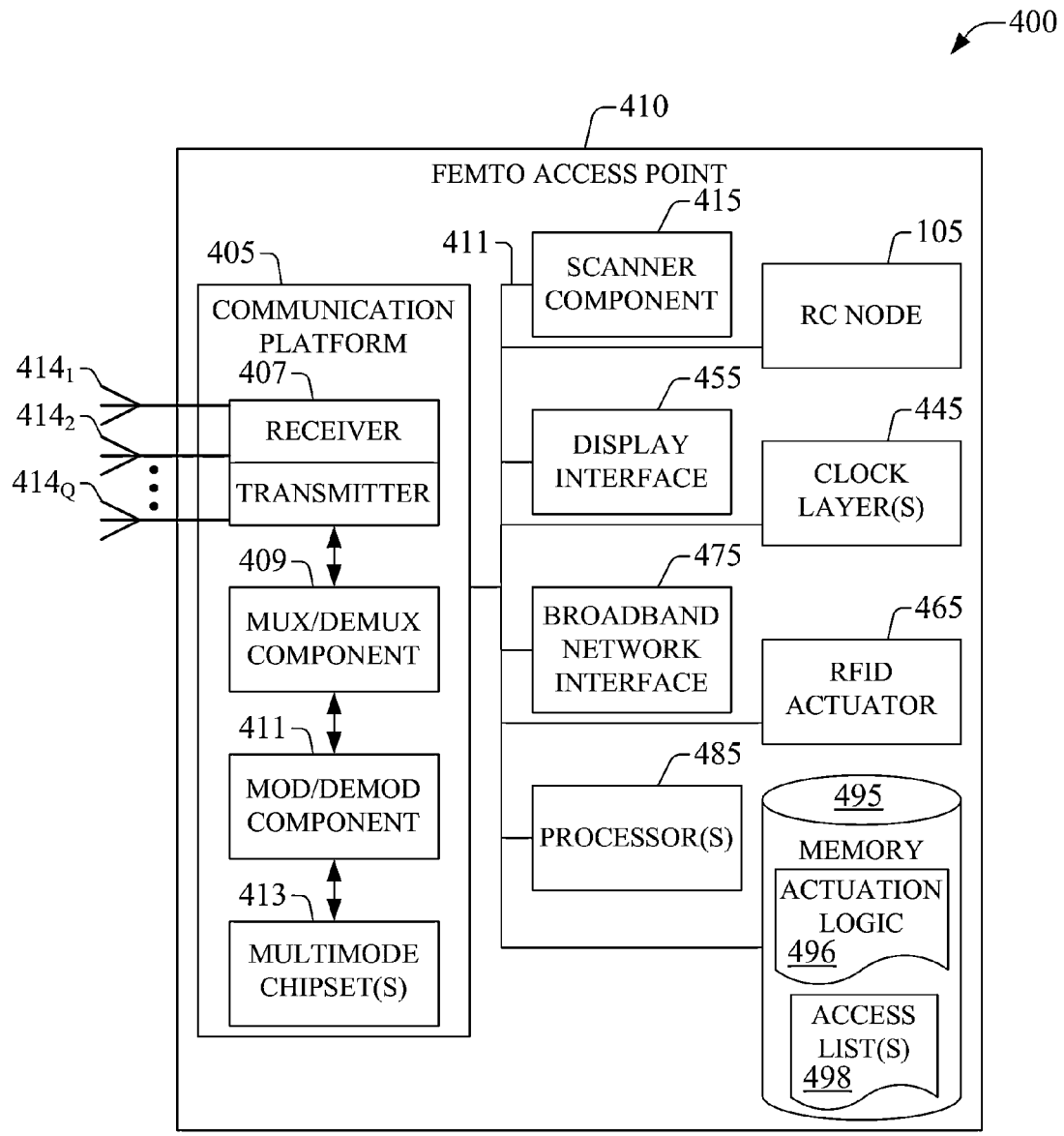
FIG. 4 illustrates an example embodiment of a femto access point that can be deployed in a femto enterprise network in accordance with aspects described herein.

FIG. 4 illustrates an example embodiment 400 of a femto access point that can be deployed in a femto enterprise network in accordance with aspects described herein. Femto AP 410 can embody one or more of femto APs $104_1$-$104_N$. In example embodiment 400, femto AP 410 can receive and transmit signal(s) from and to wireless devices like femto access points, access terminals, wireless ports and routers such as routing platform 110 and port(s) therein, or the like, through a set of antennas $414_1$-$414_Q$, with Q a natural number. The antennas $414_1$-$414_Q$ are part of communication platform 405, which comprises electronic components and associated circuitry that provide for processing and manipulation of received signal(s) and signal(s) to be transmitted. The electronic components and circuitry can include a set of one or more chipsets, e.g., multimode chipset(s) 413, that enable at least in part at least one of decoding, or deciphering, signal(s) conveyed to femto AP 410 in various disparate radio technologies, or coding of signal(s) delivered from femto AP 410 in accordance with various radio technology standards. In an aspect, communication platform 405, via at least in part multimode chipset(s) 413, can decode (i) GPS signaling such as timing messages generated, for example, by one or more deployed global navigation satellite systems (GNNSs) and relayed to femto AP 410 through a routing platform, e.g., 110 in accordance with aspects described herein; or (ii) signal(s) received from a radio frequency identification (RFID) tag upon actuation thereof.

In an aspect, communication platform 405 includes a receiver/transmitter 407 that can convert signal from analog to digital upon reception, and from digital to analog upon transmission. In addition, receiver/transmitter 407 can divide a single data stream into multiple, parallel data streams, or perform the reciprocal operation. Coupled to receiver/transmitter 407 is a multiplexer/demultiplexer 409 that facilitates manipulation of signal in time and frequency space. Electronic component 409 can multiplex information (data or traffic and control or signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 409 can scramble and spread information (e.g., codes) according to substantially any code known in the art; e.g., Hadamard-Walsh codes, Baker codes, Kasami codes, polyphase codes, and so on. A modulator/demodulator component 411 also is a part of communication platform 405, and can modulate information according to multiple modulation techniques, such as frequency modulation, amplitude modulation (e.g., M-ary quadrature amplitude modulation (QAM), with M a positive integer), phase-shift keying (PSK), and the like. In an aspect, multimode chipset(s) 413 can configure and enable mux/demux component 409 and mod/demod component to operate in accordance with protocols or standards associated various radio technologies. Processor(s) 485 also is functionally connected to communication platform 405 and can enable operations on data (e.g., symbols, bits, or chips) for multiplexing/demultiplexing, such as effecting direct and inverse fast Fourier transforms or Hadamard transforms; or modulation/demodulation of data streams.

Femto access point 410 also includes RC node 105, which can allocate radio resources, e.g., resource blocks, to a mobile device served through femto AP 410, and schedule traffic among mobile devices, and device with wireless capability, served via femto AP 410. In an aspect, RC node 105 can schedule traffic in accordance with at least one of semi-persistent scheduling, round robin, or proportional fair scheduling. Consistent with allocated radio resources, RC node 425 can select format(s) of data packet(s) and management packet(s) for traffic and signaling exchange amongst femto AP 410 and a served mobile device. In addition, RC node 105 can select a radio technology and modulation formats and coding schemes compatible therewith. In an aspect, RC node 105 can configure operation of femto AP 410 in multiple-input multiple-output (MIMO) mode of operation. Moreover, RC node 105 can determine and configure transmit power for communication effected via femto AP 410. Furthermore, RC node 105 can configure one or more of antennas $414_1$-$414_Q$ in order to attain directionality of EM radiation employed for communication, or to shape coverage area in the vicinity of femto AP 410, which can mitigate of dead-spots or weakly covered regions. Traffic and signaling can exchanged with a routing platform, e.g., 110, through RC node 105.

In embodiment 400, scanner component 415 can decode received wireless signals and thus determine at least an index that identifies a mobile device (e.g., $102_1$) attached to, or that attempts attachment to, femto AP 410 can be extracted and access can be granted or denied based at least in part on access list(s) 498. In addition, scanner component 415 can decode wireless signal(s) received as part of time-of-flight (TOF) measurements that can be employed to estimate range of a mobile device or device with wireless capability from femto AP 410. In an aspect, femto AP 410 can receive signaling that configures clock layer(s) 445 in order to conduct TOF measurements; configuration can include selection of a clock source (not shown) within clock layer(s) 425. It is noted that clock layer(s) 445 also can be configured to relay timing messages or timing information generated through an external clock. TOF measurements assess wireless signal propagation timing between a femto AP and an apparatus with wireless capability(ies); the TOF measurements can include at least one of round trip time (RTT) measurements, time or arrival (TOA) measurements, time difference of arrival (TDOA) measurements, angle of arrival (AOA) measurements, or the like.

It is noted that through at least in part communication platform 405, and multimode chipset(s) 413 therein, scanner component 415 can survey wireless signal(s) within a set of EM frequency bands that can include all EM frequency bands licensed by the service provider (e.g., personal communication services (PCS), advanced wireless services (AWS), general wireless communications service (GWCS), and so forth), all unlicensed frequency bands currently available for telecommunication (e.g., the 2.4 GHz industrial, medical and scientific (IMS) band or one or more of the 5 GHz set of bands), and all EM frequency bands in operation and not licensed to the service provider. In addition, scanner component 415 can survey wireless signal(s) over a configurable and upgradeable set of radio technologies that includes one or more of the following Wi-Fi, BlueTooth, IS-95, WiMAX, 3GPP2 UMB, Enhanced GPRS, 3GPP UMTS, 3GPP LTE, HSPA, HSDPA, HSUPA, or LTE Advanced. Processor(s) 485 can enable communication platform 405 to switch amongst radio technologies (e.g., IS-95, WiMAX . . . ) in order to effect telecommunication and enable a scan in accordance with configured demodulation and demultiplexing protocols associated with a radio technology; instructions necessary for implementation of such protocols can reside in memory 495. Such radio technology agility can afford to serve mobile devices, e.g., $102_1$ or $102_2$, that operate in disparate radio technologies, or collect pilot signal(s) modulated and coded in accordance to various technologies.

To conduct a scan, scanner component 415 exploits at least in part communication platform 405 and electronic components therein. In an aspect, scanner component(s) 212 can configure transceiver 407 to collect signal in a specific frequency carrier, e.g., frequency channel. Such configuration can allow determination of uplink (UL) carrier frequency, or channel number, associated with communication of mobile device(s) within the enterprise femto network 100 and in the vicinity of femto AP 410; and carrier frequency of downlink (DL) of disparate femto APs in the vicinity of femto AP 410. RC node 425 can deliver information that identifies carrier frequencies extracted through scanning the wireless environment of femto AP 410. Such carrier-frequency information is delivered to a routing platform, e.g., 110, which can aggregate it to form a carrier-frequency map of telecommunications within the coverage area of an enterprise femto network.

Scanner component 415 also can gather data on uplink (UL) signal strength and quality associated with a served mobile device, e.g., $102_\mu$, to effect, at least in part, handover from femto AP 410 to a disparate target femto AP. To at least that end, scanner component 415 can gather UL sounding signal(s) and analyze such signal(s) to determine DL channel quality or strength; analysis can be enabled at least in part via processor(s) 485. In an aspect, signal strength can be determined through received signal strength indicators (RSSIs) or received signal code power (RSCP), while quality can be assessed through metrics such as signal-to-noise ratio (SNR), signal-to-noise-and-interference ratio (SNIR), or energy per chip over total received power ($E_c/N_0$).

In addition, femto AP 410 includes display interface 455, which can render functions that control functionality of femto AP 410 or reveal operational conditions thereof. In addition, display interface 1812 can include a screen to convey information to an end user. In an aspect, display interface 455 can be embodied in a liquid crystal display (LCD), a plasma panel, a monolithic thin-film based electrochromic display, or the like. Moreover, display interface 455 also can include a component (e.g., speaker(s)) that facilitates communication of aural indicia, which can be employed in connection with messages that convey operational instructions to an end user or consumer. Display interface 1812 also can enable data entry (e.g., through a linked keypad or via touch gestures), which can allow femto AP 410 to receive external commands, such as restart operation, flush a memory or buffer, configure an access list, etc.

Broadband network interface 475 enables connection of femto AP 410 to a routing platform, as described herein, through broadband link(s) such as link(s) $114_\lambda$, which can enable incoming and outgoing data and signaling flow. In an aspect, broadband network interface 475 can include a port component with substantially the same or the same functional aspects or features as port component 315. Broadband network interface 1814 can be internal or external to femto AP 1805, and it can utilize display interface 1812 for at least one of end-user interaction or status information delivery. Processor(s) 485 can configure at least in part operation of one or more port(s), e.g., switching voltages in a dry contact or assignment of a logical address such as an IP address to a port, that can reside within broadband network interface 475. It is noted that RC node 425 can conduct at least part of the assignment of logical address(es) to a port within broadband network interface.

Femto AP 410 also includes an RFID actuation component 465, also termed herein RFID actuator 465, which can convey through communication platform 405 specific control packets within a pilot signal in order to stimulate an RFID tag and retrieve information therein by decoding RF packet(s) received from the RFID tag in response. Actuation protocol(s) and code sequence hypotheses for decoding information retained in an RFID tag can be included in actuation logic 496 stored in memory 495.

Memory 495 can retain data structures, code instructions and program modules, or substantially any type of software or firmware; system or device information; code sequences hypotheses, and modulation and multiplexing hypotheses; spreading and pilot transmission; femto AP floor plan configuration; and so on. Additionally, memory 495 can retain content(s) (e.g., multimedia files, subscriber-generated data); security credentials (e.g., passwords, encryption keys, digital certificates, biometric reference indicators like voice recordings, iris patterns, fingerprints); or the like.

Processor(s) 485 is functionally connected, through bus 411 to component(s), platform, interface(s), layer(s) and substantially any or any functional element that resides within femto AP 410. Bus 411 can be embodied in at least one of a memory bus, a system bus, an address bus, or one or more reference link(s) or interface(s). In an aspect, processor(s) 485 is functionally coupled, e.g., via a memory bus within at least a portion of bus 411, to memory 495 in order to store therein and retrieve there from information to operate or confer functionality to the components, platform, interface (s), layer(s) and substantially any or any functional element that reside within femto AP 410.

Figure 5:
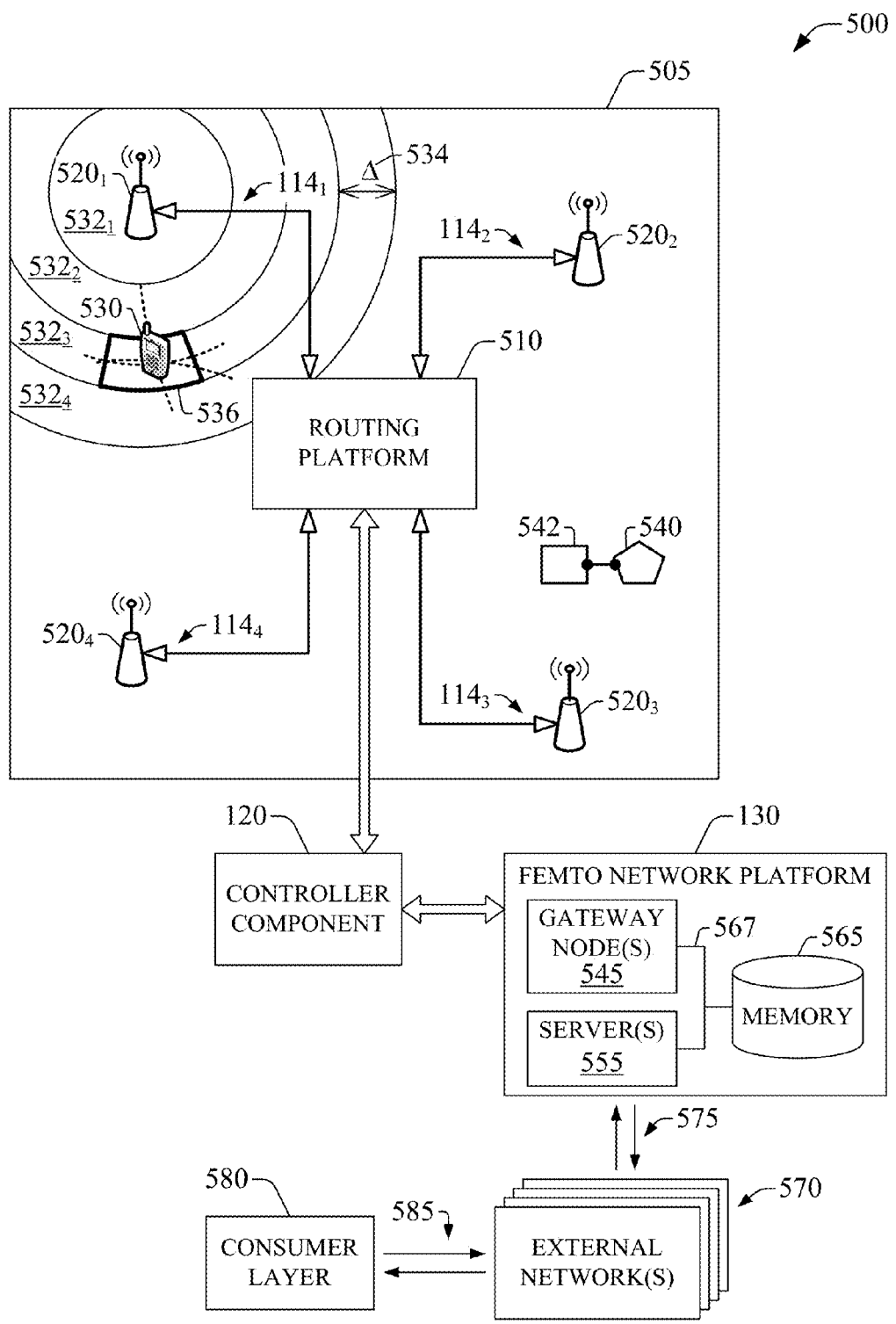
FIG. 5 illustrates a diagram of an example embodiment of a femto enterprise network architecture that enables collection of location data in accordance with aspects of the subject innovation.

FIG. 5 illustrates a diagram of an example embodiment 500 of an enterprise femto network that enables collection of location data and utilization thereof in accordance with aspects of the subject innovation. Location data can include location estimate(s) of a mobile device or an entity linked to an apparatus with wireless capability. Routing platform 510 can configure, e.g., synchronize, a clock layer in each of femto APs $520_1$-$520_4$, and control, e.g., trigger or initiate, terminate, etc., time-of-flight (TOF) measurements of propagation timing of wireless signal(s), such as control signal(s), that can enable estimate(s) of distance of a mobile device (e.g., mobile 430) or an apparatus with wireless capability (e.g., 542) from one or more of femto APs $520_1$-$520_4$. Such distance, or range, estimates can allow routing platform 510 to resolve a location estimate for mobile device 530 or an apparatus 542 with wireless capability. As an example, routing platform 510 can triangulate a position of mobile device 530—dotted lines near and through mobile 530 indicate triangulation effected through femto APs $520_1$, $520_2$, and $520_3$. In addition, routing platform 510 can triangulate a position of apparatus 542 and thus produce an estimate of the position of an entity 540 linked spatially with the apparatus; for instance, the entity can be a vehicle and a navigation device thereof can be apparatus 542. A memory within routing platform 510 can retain criteria to determine whether the entity 540 spatially linked to the apparatus 542. It is noted that in a femto enterprise network that is deployed within multiple coverage areas, see example embodiment 250, a location estimate can be generated through range estimates generated via timing measurements performed by at least four femto APs. As an illustration, TOF measurements performed at least in part via femto AP $520_1$ can result in a set of TOF-bands or fringes $532_1$-$532_4$. The width Δ 532 of a TOF band is determined primarily through a timing advance (TA) established by a clock source that determines chip structure linked to the pilot wireless signal(s). It is noted that while not displayed, other femto APs also can generate a TOF-band structure as the one related to femto AP $520_1$.

Location estimate(s) can be conveyed to a consumer layer 580, which can utilize the location estimate(s) as part of a navigation or location-based service. Routing platform can deliver the location estimate(s) as at least one of a short message service (SMS) communication, an unstructured supplementary service data (USSD) message, an email communication, an instant message. In an aspect, to delivery of a location estimate proceed at least in part as described supra in connection with communication of content to femto network platform 130. A gateway node that is part of gateway node(s) 545 can communicate the location estimate to a gateway node within the external network(s) 570, which can relay the location estimate to a serving node therein in order to delivery the location estimate to the consumer layer 580. In an aspect, external network(s) 570 can be an IMS network or almost any or any packet-switched network.

Consumer layer 580 can include one or more devices operated by one or more subscribers or prosumers. As an example, consumer layer can be a mobile device associated with an owner or leaser of entity 540. In a scenario, coverage area 505 can be a parking lot, either multi-floor or single-floor, and entity 540 can be a vehicle for which routing platform 510 generates a location estimate at the time the vehicle is parked. The location estimate for the parked vehicle can be provided to consumer layer based upon various criteria such as when a registered mobile device re-enters the parking lot after the vehicle has been parked. Alternatively or additionally, the location estimate can be supplied upon demand from a subscriber associated with the vehicle and that operates a mobile device, demand for the location estimate of the vehicle can be effected by dialing a specific phone number extension for routing platform 510, delivering a SMS message or an email message, or a USSD code. As another example, consumer layer 580 can be equipment of a law enforcement agency and location estimate(s) can be supplied as part of the Communications Assistance to Law Enforcement Act (CALEA). In a scenario, a black list consisting of one or more unique identifiers for respective wireless devices can be supplied through an interface (not shown) in consumer layer 580. Routing component 510 can retain the black list in a memory, e.g., in access list(s) in example embodiment 600. When a black listed mobile device attempts attachment to a femto AP that is part of femto enterprise network, routing component 510 can alert the law enforcement equipment in consumer layer 580, for example, by delivering the location estimate of the detected blacklisted mobile device. In addition or as an alternative, when the blacklisted mobile device is detected, routing platform 510 can track location of the blacklisted mobile device within coverage area 505.

In an aspect of the subject innovation, to utilize high pilot transmit power to increase the number of femto APs that generate range estimates to implement triangulation, routing platform 510 can configure delivery and transport of control signal(s) employed at least in part in TOF measurements in channel(s), or frequency carrier(s), disparate from those utilized for traffic. It should be appreciated that utilization of dedicated carriers for triangulation that are disparate, e.g., orthogonal, to carriers employed for voice and data can mitigate interference that may be incurred through generation of location estimates. As an example, femto APs can convey pilot signal(s) for TOF measurements in a carrier within unlicensed electromagnetic (EM) radiation bands, whereas the femto APs can convey voice and data in a channel within a licensed EM radiation band.

Figure 6:
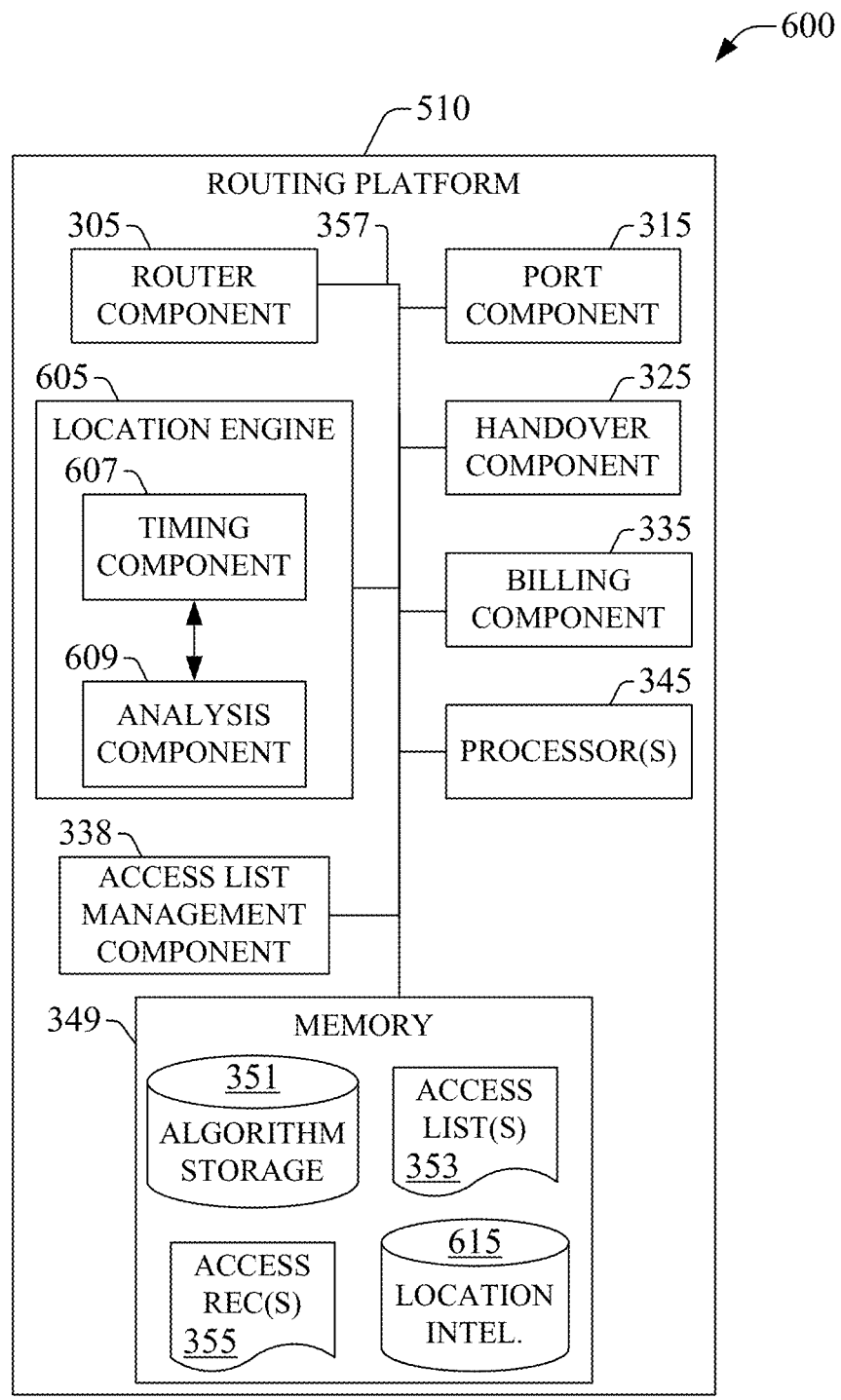
FIG. 6 illustrates a block diagram of an example embodiment of a routing platform that is part of an enterprise femto network architecture in accordance with aspects disclosed herein.

In an example embodiment of routing platform 510, illustrated in FIG. 6, location engine 605 can generate location estimate(s) through triangulation. To at least that end, timing component 607 enable routing component 510 to configure and control the TOF measurements, and analysis component 609 exploits data collected through the timing measurements to compute a location estimate through triangulation; algorithm storage 351 can retain code instructions that, when executed, implement triangulation. In an aspect, analysis component 419 can select a propagation model, retained within algorithm storage to include stochastic aspects of propagation such as multipath or other scattering, shadowing, or path loss, in a computation of a location estimate. Location estimate(s) can be retained in location intelligence 615.

Routing component 510 also can control complexity of timing configuration(s), e.g., selection of clock sources adequate for coarse resolution or fine resolution of location estimates, based at least in part on a hierarchy of resolution of generated location estimate(s) and aspects of an associated location service. (1) For specific content routing, e.g., off-loaded content from a wide area network (WAN) to the enterprise femto coverage area 505, association of a unique identifier (ID) for the serving femto AP with mobile device 530 or a unique ID thereof can be sufficient; one or more of external network(s) 570 can embody the WAN. In example embodiment 600, location intelligence 615 can include a mapping of unique femto ID(s) linked to each provisioned femto AP and a deployment configuration of femto APs such as $520_1$-$520_4$. (2) To implement, at least in part, location-based handover from a first femto AP to a second femto AP, routing component 510 can select a clock source that provides a TOF-bandwidth $\Delta$ 534 that is smaller than a characteristic spacing $\Delta'$ among provisioned femto APs that can enable the handover; for instance, $\Delta/\Delta'$=0.1 can be utilized. In example embodiment 600, selection of the clock source can be implemented at least in part through timing component 607. As an example, $\Delta'$ can be determined as an average of nearest-neighbor distances among femto APs. In addition, azimuth resolution can be implemented to further refine a location estimate to a specific tile in order to distinguish among substantially equally or equally close femto APs that are candidate for handover. Azimuth-resolved timing measurements, e.g., AOA in combination with RTT, can determine a tile such as 536 (indicated with thick lines) rather than a TOF-band, e.g., $532_3$. It should be appreciated that a set of two or more antennas in a femto AP, such as $520_1$, can be configured, by routing component 510, and employed to afford azimuth resolution; timing component 607 can enable at least in part such configuration. (3) For tracking of a mobile device 530 or an entity 540 associated to an apparatus 540 with wireless capabilities, finer resolution is necessary in order to enable triangulation of the mobile device 530 or the apparatus 540 to extract a location estimate that is highly accurate, e.g., with a resolution of the order of 1 m. To allow high-resolution triangulation, routing platform 510 can select a clock source that provides timing advance (TA) such that $\Delta$ 534 is sufficiently narrow, e.g., 1 m, to afford highly-resolved triangulation. In example embodiment 600, timing component 607 can select the clock source. Location estimate(s) can be retained in a memory that is part of routing component 510, and can be conveyed within the bounds of the coverage area of the enterprise femto network or outside such bounds.

Routing component 510 can exploit artificial intelligence (AI) or machine learning methods to infer (e.g., reason and draw a conclusion based upon a set of metrics, arguments, or known outcomes in controlled scenarios) a satisfactory or optimal timing resolution to generate a location estimate with a spatial resolution suitable to a predetermined location service. Inference can be based at least in part upon cost-utility analysis that determines the trade off between signaling cost, e.g., clock selection, triggering signaling, carrier selection and communication, versus the benefit of accurately knowing position of mobile device. In embodiment 600, timing component 607 can implement the cost-utility analysis. Machine learning methods can be retained in algorithm storage 351.

Artificial intelligence techniques typically apply advanced mathematical algorithms—e.g., decision trees, neural networks, regression analysis, principal component analysis (PCA) for feature and pattern extraction, cluster analysis, genetic algorithm, or reinforced learning—to a data set. In particular, handover component 254 or any component(s) therein can employ one of numerous methodologies for learning from data and then drawing inferences from the models so constructed. Such methodologies can be retained in memory 260. For example, Hidden Markov Models (HMMs) and related prototypical dependency models can be employed. General probabilistic graphical models, such as Dempster-Shafer networks and Bayesian networks like those created by structure search using a Bayesian model score or approximation can also be utilized. In addition, linear classifiers, such as support vector machines (SVMs), non-linear classifiers like methods referred to as "neural network" methodologies, fuzzy logic methodologies can also be employed. Moreover, game theoretic models (e.g., game trees, game matrices, pure and mixed strategies, utility algorithms, Nash equilibria, evolutionary game theory, etc.) and other approaches that perform data fusion, etc., can be exploited.

Figure 7A:
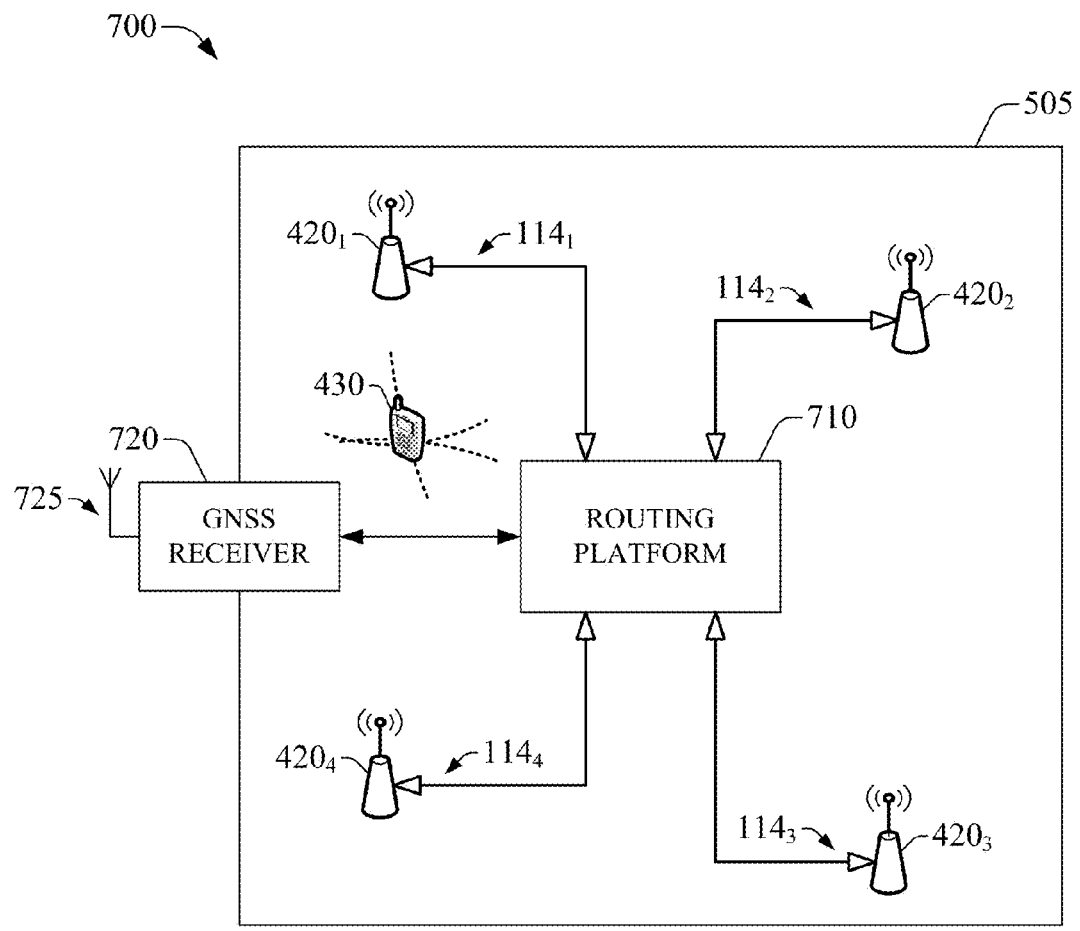
FIGS. 7A and 7B illustrates diagrams of example embodiments of a femto enterprise network architecture that enables collection of location data of a mobile in accordance with aspects of the subject innovation.

FIG. 7A illustrates a diagram 700 of a femto enterprise network architecture that enables collection of location data of a mobile in accordance with aspects of the subject innovation. Routing platform 610 receives timing messages, or timing reference(s), from a global navigation satellite system (GNNS) receiver component 620, also termed herein as GNSS receiver 620, which can collect timing messages from one or more satellites through one or more antenna(s) 625. In an aspect, GNSS receiver 620 can be exposed to open sky, and at least a part thereof can reside within a NID, e.g., NID $210_2$. Femto APs $520_1$-$520_4$ can time-stamp control message(s) or sounding signal(s) conveyed by mobile device 430 and thus generate range estimate(s) that allow generation of location estimates based at least in part on triangulation.

Figure 7B:
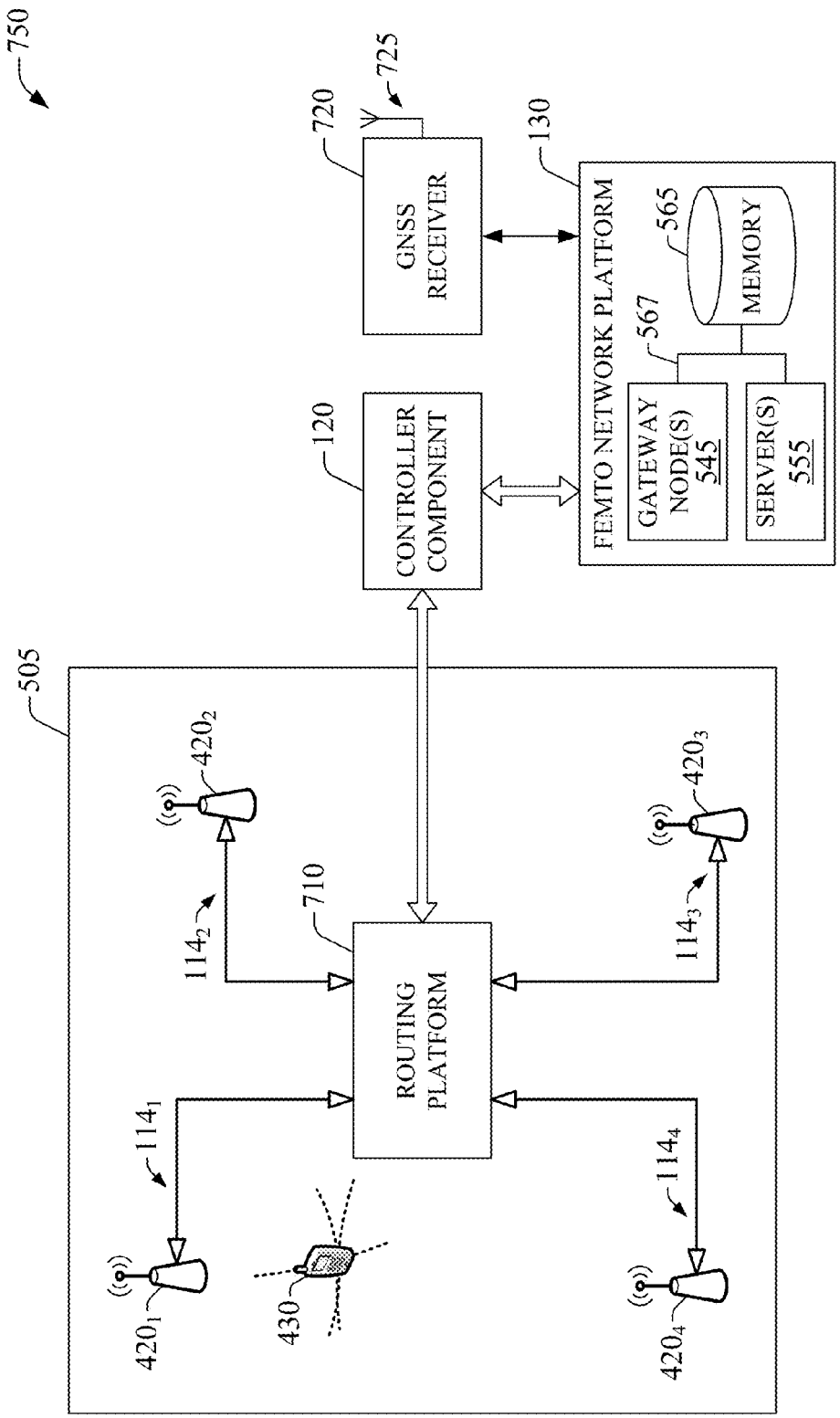

FIG. 7B displays a diagram of an embodiment 650 of a femto enterprise network architecture that enables collection of location data of a mobile in accordance with aspects of the subject innovation. In an aspect, timing message(s) GNSS receiver 620 is functionally connected to femto network platform 660, which can relay the timing message(s) via gateway node(s) 545. It should be appreciated that GNSS receiver 620 can be part of assisted GPS (AGPS) infrastructure provided by a network operator that administer femto network platform 660 and femto APs $520_1$-$520_4$.

Figure 8:
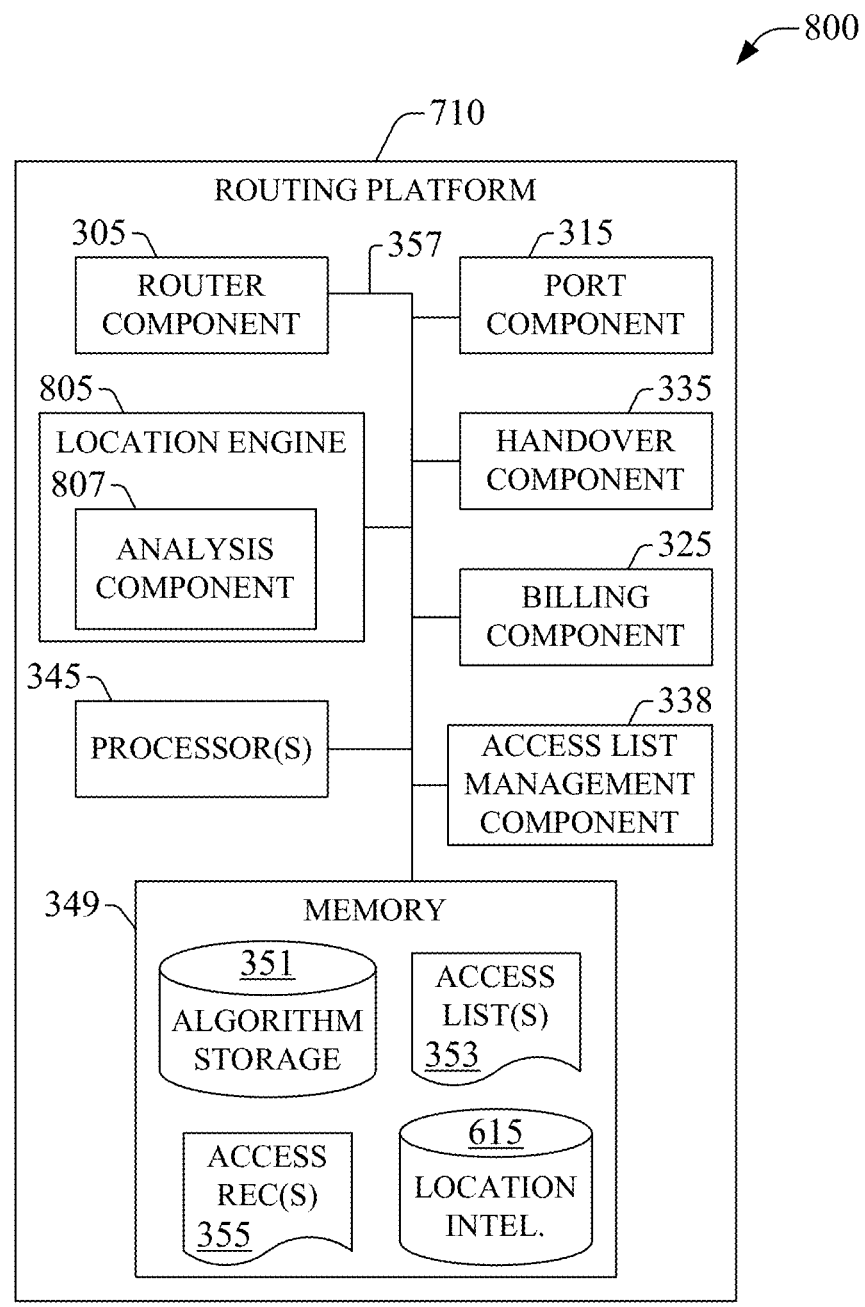
FIG. 8 illustrates an example embodiment of a routing platform that can be part of an enterprise femto network architecture in accordance with aspects of the disclosure.

In embodiments 700 and 750, routing platform 710 exhibits less complexity than routing platform 510. As illustrated in FIG. 8, location engine 805 does not include a timing component, but rather location engine 805 operates as a pass-through of timing message(s) received from GNSS receiver 720. Analysis component 807 can operate in substantially the same manner as analysis component 809. In particular, analysis component 807 can receive timing signaling, e.g., records of time-stamped messages, originated at a plurality of femto APs and utilize such signaling to perform triangulation and associated location estimate(s) of mobile device 530.

Figure 9:
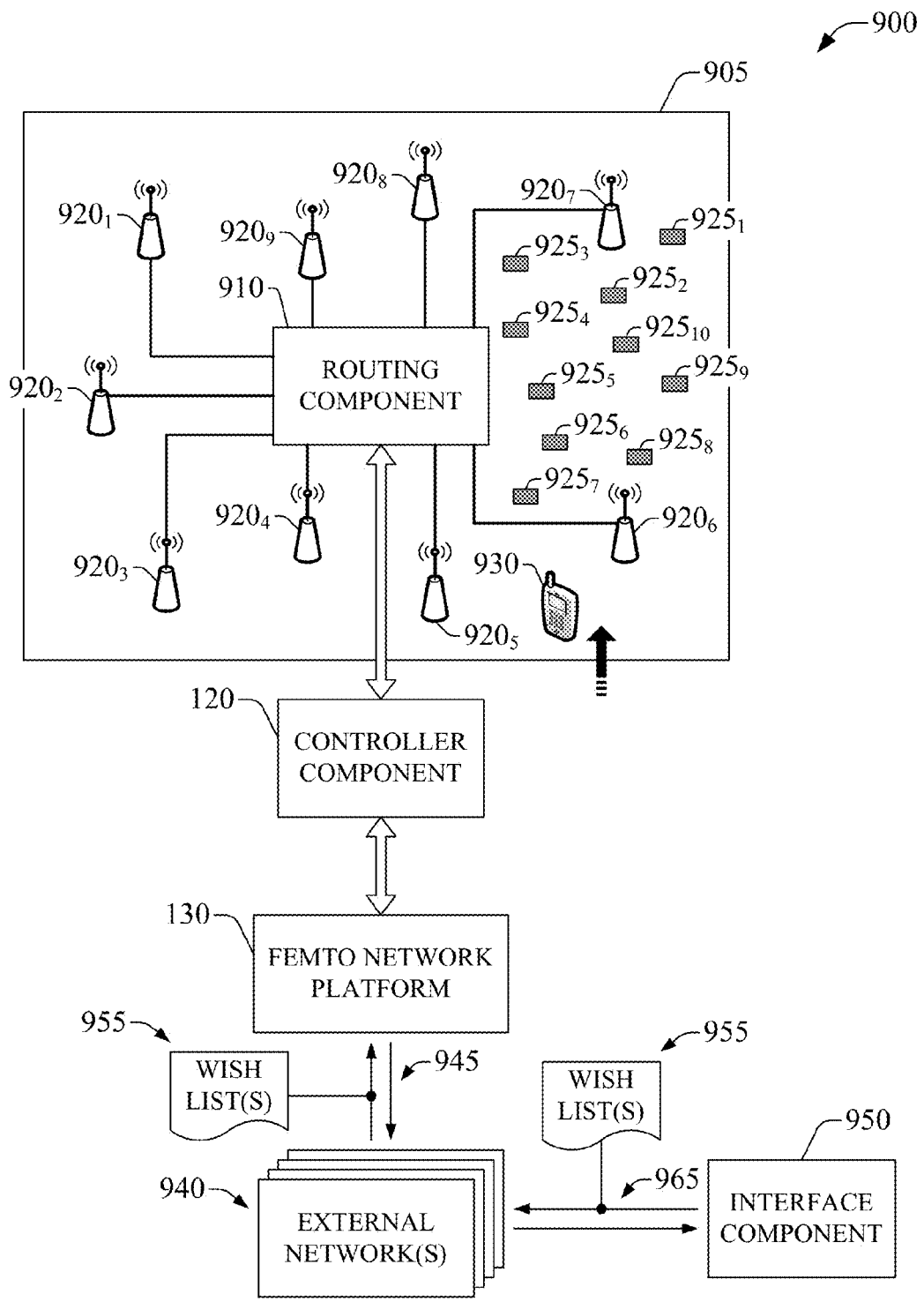
FIG. 9 represents an example system that enables customized item navigation at least in part through example femto network architecture in accordance with aspects described herein.

FIG. 9 represents an example system 900 that enables customized item navigation at least in part through an example femto network architecture in accordance with aspects described herein. Interface component 950 enables a subscriber or prosumer to configure wish list(s) 955 of items to be identified within a remote site 905 that includes an enterprise femto network architecture. Interface component can deliver wish list 955 through link(s) 955, which can be broadband backhaul link(s), to external network(s) 940. For instance, external network(s) can be a broadband non-mobile network that provides internet service. External network(s) 940 can convey wish list(s) 955 to femto network platform 130, which can relay the wish list(s) 955 to controller node 120—e.g., a radio network controller in a 3GPP UMTS telecommunication architecture.

Controller component 120 can deliver the wish list(s) 955 to routing component 910, which can generate a set of locations of item(s) listed in wish list(s) 955 for which RFID tag(s), e.g., $925_1$-$925_{10}$, are contacted to the item(s). Accordingly, the generated set of location estimate(s) can be mapped to the tagged item(s). In an aspect, routing component 910 can resolve location estimates for the item(s) in the wish list(s) 955 in response to entrance of mobile device 930 into the coverage area 905 of the enterprise femto network, and attachment of the mobile device 930 to a femto AP therein; wherein mobile device 930 is linked to the subscriber or prosumer that configured the wish list(s) 955. Alternatively or additionally, routing component 910 can generate the set of location estimate(s) in accordance with at least one of a schedule, retained as part of location intelligence, e.g., 615, within of routing platform 910; or an event such as a relocation or RFID tags $925_1$-$925_{10}$ within coverage area 905.

Figure 10:
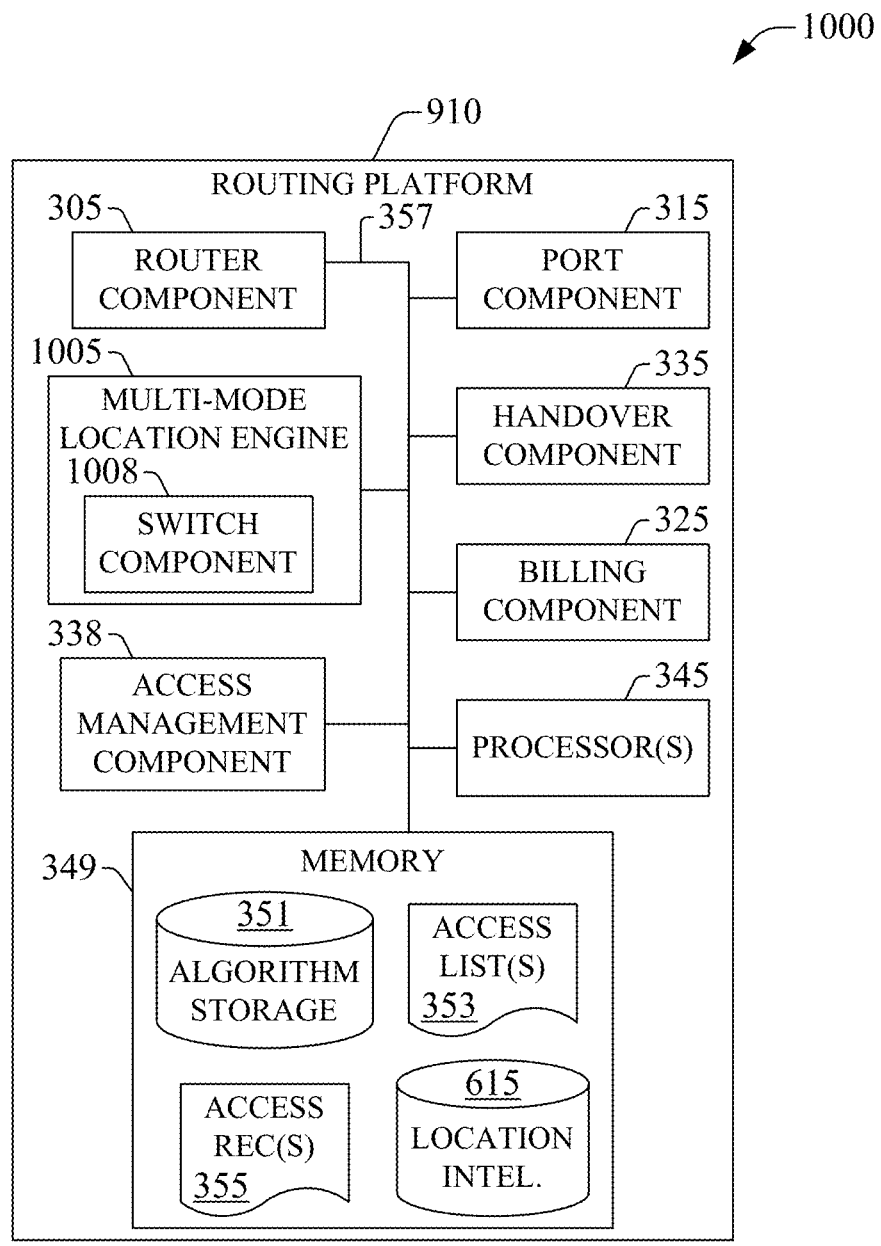
FIG. 10 illustrates an example embodiment of a routing platform that can operate within an enterprise femto network in accordance with aspects described herein.

Generation of location estimates for items within wish list 955 can be accomplished at least in part through RFID actuator 465, which can remotely probe the RFID tag(s) $925_1$-$925_{10}$ via pilot signal(s) delivered through a set of femto APs, e.g., $920_6$, $920_7$, and $920_8$. Probing of RFID tag(s) can enable triangulation of each tag and thus generation of respective location estimate(s); triangulation can be implemented via a location engine within routing component 910 in accordance at least in part with aspects described herein. In an example embodiment 1000 of routing platform 910, illustrated in FIG. 10, a multi-mode location engine 1005 can perform triangulation of location of an RFID tag. Multi-mode location engine 1005 includes a switch component 1008 that can toggle functionality of the multi-mode location engine based at least in part on timing capabilities of routing platform 910. In an aspect, when routing platform 910 can supply timing configuration to one or more femto APs, switch component 1008 can configure operation of multi-mode location engine in a mode of operation substantially the same or the same as location engine 605. Alternatively, when routing platform 910 exploits external timing information to configure timing of a set of femto APs that provide wireless service to the enterprise femto network, switch component 1008 can set multi-mode location engine to operation that is substantially the same or the same as location engine 805. It should be appreciated that that multi-mode location engine 1005 includes analysis component 807 (not shown in FIG. 10), and timing component 607 and analysis component 609 (neither one shown in FIG. 10).

Femto AP(s) $920_1$-$920_9$ can include RFID actuation logic, e.g., 496, retained in a memory therein, that enables delivery of a pilot signal to an RFID tag and performs TOF measurement(s) to collect timing data and allow triangulation. The pilot signal can be conveyed in a frequency carrier disparate from a band of EM radiation employed for communication through the femto AP(s); thus, RFID tag(s) $825_1$-$825_{10}$ can be interrogated without inflicting substantive interference. Femto AP(s) also can decode information retained in the interrogated RFID tag(s), and relay such information to routing platform 810, which can perform at least one of the following: retain the information in memory, e.g., memory 349, or adjust the information. It is noted that the information can include at least one of product identification or pricing thereof. In an aspect, adjustment of information can be directed to adjusting pricing of the item(s) identified through the probed RFID tag(s).

In view of the example systems described above, example methods that can be implemented in accordance with the disclosed subject matter can be better appreciated with reference to flowcharts in FIGS. 10-18. For purposes of simplicity of explanation, example methods disclosed herein are presented and described as a series of acts; however, it is to be understood and appreciated that the claimed subject matter is not limited by the order of acts, as some acts may occur in different orders and/or concurrently with other acts from that shown and described herein. For example, one or more example methods disclosed herein alternatively or additionally can be represented as a series of interrelated states or events, such as in a state diagram. Moreover, interaction diagram(s) may represent methods in accordance with the disclosed subject matter when disparate entities enact disparate portions of the methodologies. Furthermore, not all illustrated acts may be required to implement a described example method in accordance with the subject specification. Further yet, two or more of the disclosed example methods can be implemented in combination with each other, to accomplish one or more features or advantages herein described. It should be further appreciated that the example methods disclosed throughout the subject specification are capable of being stored on an article of manufacture to facilitate transporting and transferring such methodologies to computers for execution, and thus implementation, by a processor or for storage in a memory.

Figure 11:
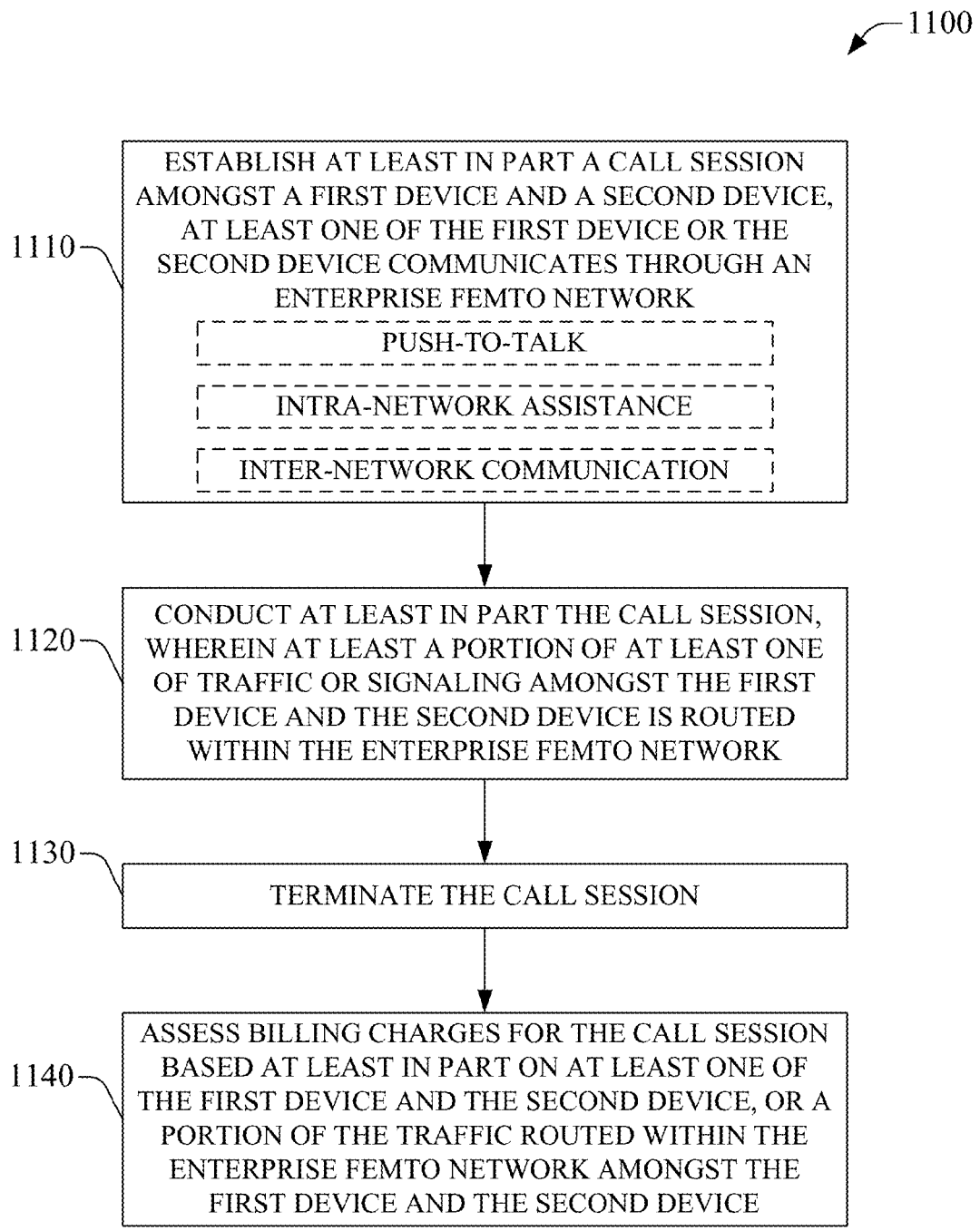
FIG. 11 displays a flowchart of an example method for communicating within a femto mesh network according to aspects disclosed in the subject specification.

FIG. 11 displays a flowchart of an example method 1100 for communicating within a femto mesh network according to aspects disclosed in the subject specification. A routing platform or one or more component therein can enact, or implement, the subject example method 1100. Alternatively or additionally, one or more processors that confer at least part of the functionality of the routing platform can effect the subject example method 1100. At act 1110, a call session is established, at least in part, amongst a first device and a second device. At least one of the first device or the second device communicates through an enterprise femto network. In an aspect, the first device or the second device can be mobile device(s); however, either the first device or the second device can be a stationary device with wireless capabilities, such as a printer, a digital video recorder (DVR) box, an IPTV tuner, a fridge, or the like. In another aspect, the call session can be a push-to-talk session; and intra-network assistance session, wherein either the first of second device is an apparatus that enables customer support; or an inter-network communication. At act 1120, the call session is conducted at least in part, wherein at least a portion of at least one of traffic or signaling amongst the first device and second device is routed within the enterprise femto network. At act 1130, the call session is terminated. Termination can include releasing radio resources allocated within one or more femto APs that enabled, at least in part, the communication amongst the first and second device. In addition, reassigning routing path configuration(s) such as logical addresses, and deactivating radio bearers and packet data protocol (PDP) context(s) also can be included in termination of the call session. Moreover, data buffers or caches can be flushed as part of termination of the call session. At act 1140, billing charges are assessed for the call session based at leas in part on at least one of the first device and the second device, or a portion of the traffic or signaling routed within the enterprise femto network amongst the first device and the second device. Billing charges also can be assessed at least in part based on at least one of customer segments associated, respectively with the first and second device; or promotional campaign(s) related to utilization of enterprise femto network.

Figure 12:
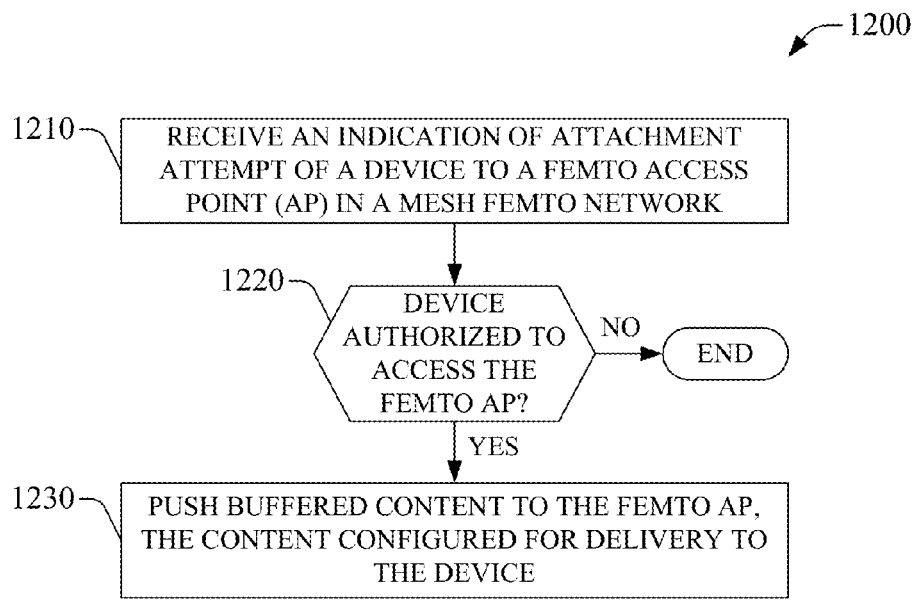
FIG. 12 represents a flowchart of an example method for delivering content within a femto mesh network according to aspects described herein.

FIG. 12 represents a flowchart of an example method 1200 for delivering content within a femto mesh network according to aspects described herein. A routing platform or one or more component therein can enact, or implement, the subject example method 1200. Alternatively or additionally, at least one or more processors that confer at least part of the functionality of the routing platform can effect the subject example method 1200. At act 1210, an indication of attachment attempt of a device to a femto AP in a mesh femto network is received. At act 1220, it is determined if the device is authorized to access the femto AP. In the negative case, the subject example method ends. Conversely, buffered content is pushed to the femto AP at act 1230. The content is configured for delivery to the device; as an example, the content can be a set of digital item(s) such as song album(s), games, books, collection(s) of published articles, or movies, which can be resource-intensive to download OTA. Content can be tagged for delivery to the device by a network operator that administers the femto mesh network at the time of sale of the content(s).

Figure 13:
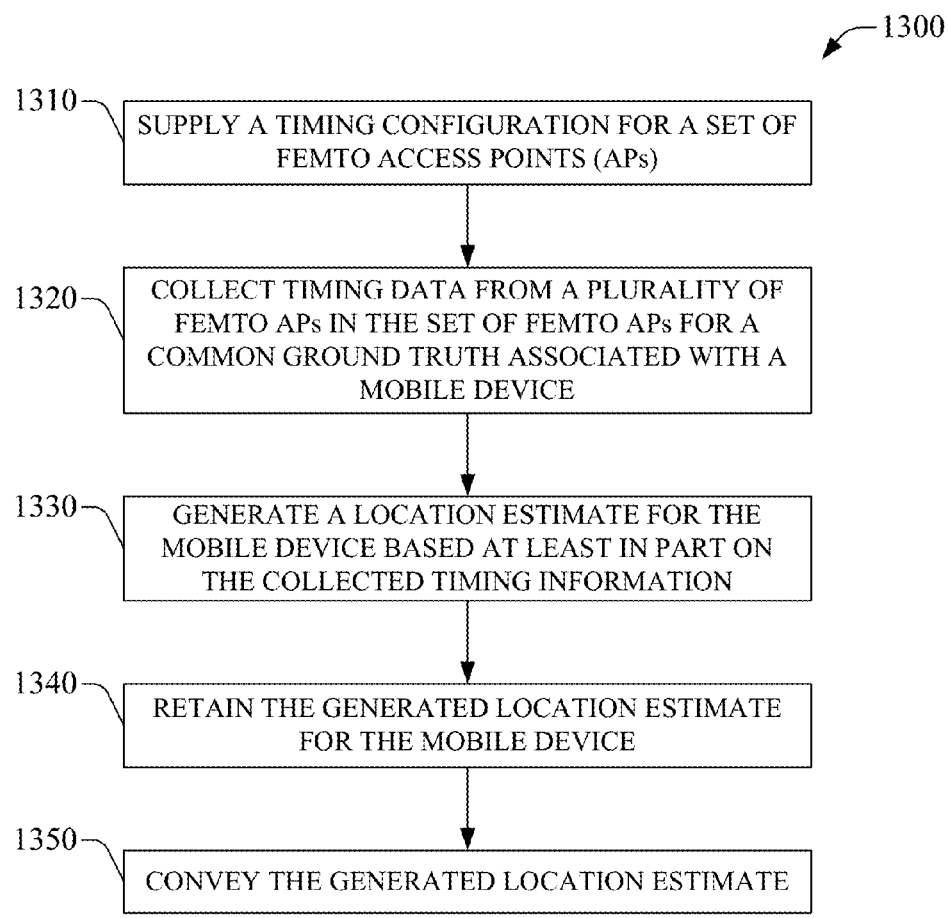
FIG. 13 is a flowchart of an example method for locating a mobile device that operates within a femto network according to aspects described herein.

FIG. 13 is a flowchart of an example method 1300 for locating a mobile device that operates within an enterprise femto network according to aspects described herein. One or more network components within a routing platform can enact, or implement, the subject example method 1300. Alternatively or additionally, at least one or more processors that confer at least part of the functionality of the routing platform can effect the subject example method 1300. At act 1310, timing configuration for a set of femto APs is supplied. Timing configuration can be based on at least one of a set of clock sources selected, for example, through a timing component (e.g., component 407); or timing message(s) generated via a GNSS receiver (e.g., receiver 720). At act 1320, timing data, or propagation timing data, from the set of femto APs is collected for a common ground truth associated with a mobile device. At act 1330, a location estimate for the mobile device is generated based at least in part on the collected timing information, or timing data. At act 1340, the generated location estimate for the mobile device is retained. At act 1350, the location estimate is conveyed.

Figure 14:
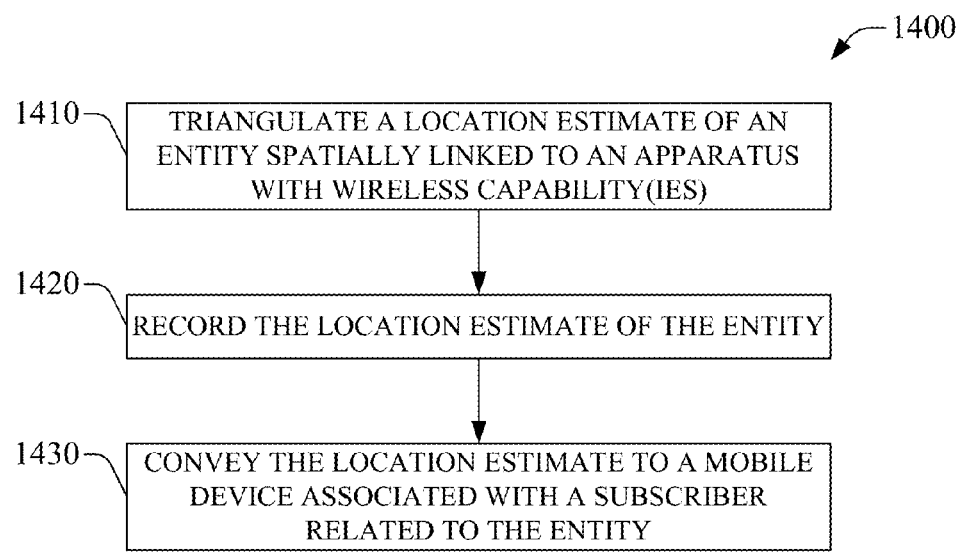
FIG. 14 displays a flowchart of an example method for identifying a location of an entity according to aspects described herein.

FIG. 14 displays a flowchart of an example method 1400 for location identification of an entity according to aspects described herein. One or more network components within a routing platform can enact, or implement, the subject example method 1400. Alternatively or additionally, at least one or more processor(s) that confer at least part of the functionality of the routing platform can effect the subject example method 1400. At act 1410, a location estimate of an entity spatially linked to an apparatus with wireless capability(ies) is triangulated. Criteria to determine if the entity is spatially linked to the apparatus can be established by the one or more networks that can enact the subject example method. At act 1420, the location estimate of the entity is recorded. At act 1430, the location estimate of the entity is conveyed to a mobile device associated with a subscriber related to the entity. The location estimate can be delivered as at least one of a short message service (SMS) communication, an unstructured supplementary service data (USSD) message, or as part of a navigation or location-service application executed in the mobile device.

Figure 15:
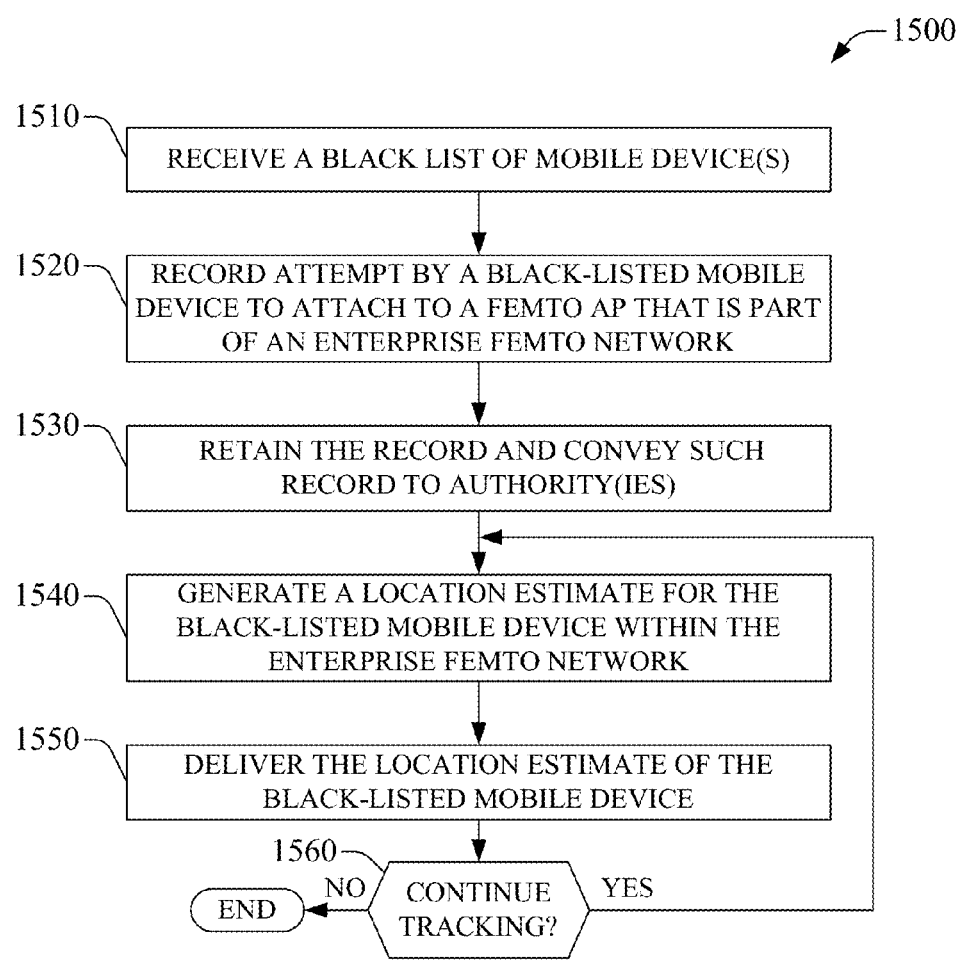
FIG. 15 displays a flowchart of an example method for tracking a location estimate for selected mobile device(s) according to aspects described herein.

FIG. 15 displays a flowchart of an example method for tracking a location estimate for selected mobile device(s) according to aspects described herein. A routing platform or one or more component therein can enact, or implement, the subject example method 1500. Alternatively or additionally, one or more processors that confer at least part of the functionality of the routing platform can effect the subject example method 1500. In an aspect, the subject example method can be part of mechanism for information delivery associated with the Communications Assistance to Law Enforcement Act (CALEA). At act 1510, a black list of mobile device(s) is received. As an example, the mobile device(s) can be an ankle shackle with wireless capability attached to an individual that is a fugitive. As another example, mobile device can be user equipment of a person restricted from accessing the coverage area of an enterprise femto network. As a further example, mobile device(s) can be a subscriber station associated with one or more assailant(s) in a hostage situation within the coverage area of the enterprise femto network. At act 1520, an attempt by a blacklisted device to attach to a femto AP that is part of an enterprise femto network is recorded. Attempted attachment can be part of pilot signal(s) transmission while the blacklisted device is in idle mode, and detection of the pilot signal(s) by the femto AP. At act 1530, the record is retained and conveyed to authority(ies). In an aspect, the authority(ies) can be at least one of one or more law enforcement agencies, or a set of emergency first responders (e.g., paramedics, police officers, special weapons and tactic (SWAT) units).

At act 1540, location of the blacklisted device within the enterprise femto network is generated. In an aspect, generation of the location estimate can proceed in accordance with example subject method 1000. At act 1550, location estimate of the blacklisted device is delivered. As an example, location can be delivered to one or more wearable devices, e.g., a helmet-mounted display, that are part of law-enforcement officers or first emergency responders operations gear or equipment. As another example, location estimate can be provided to an operation control center related to the authority(ies). At act 1560, it is determined if location tracking is to be continued. Various criteria can be employed to determine continuation of location tracking. In the affirmative case, flow is directed to act 1540. Conversely, the subject example method is terminated.

Figure 16:
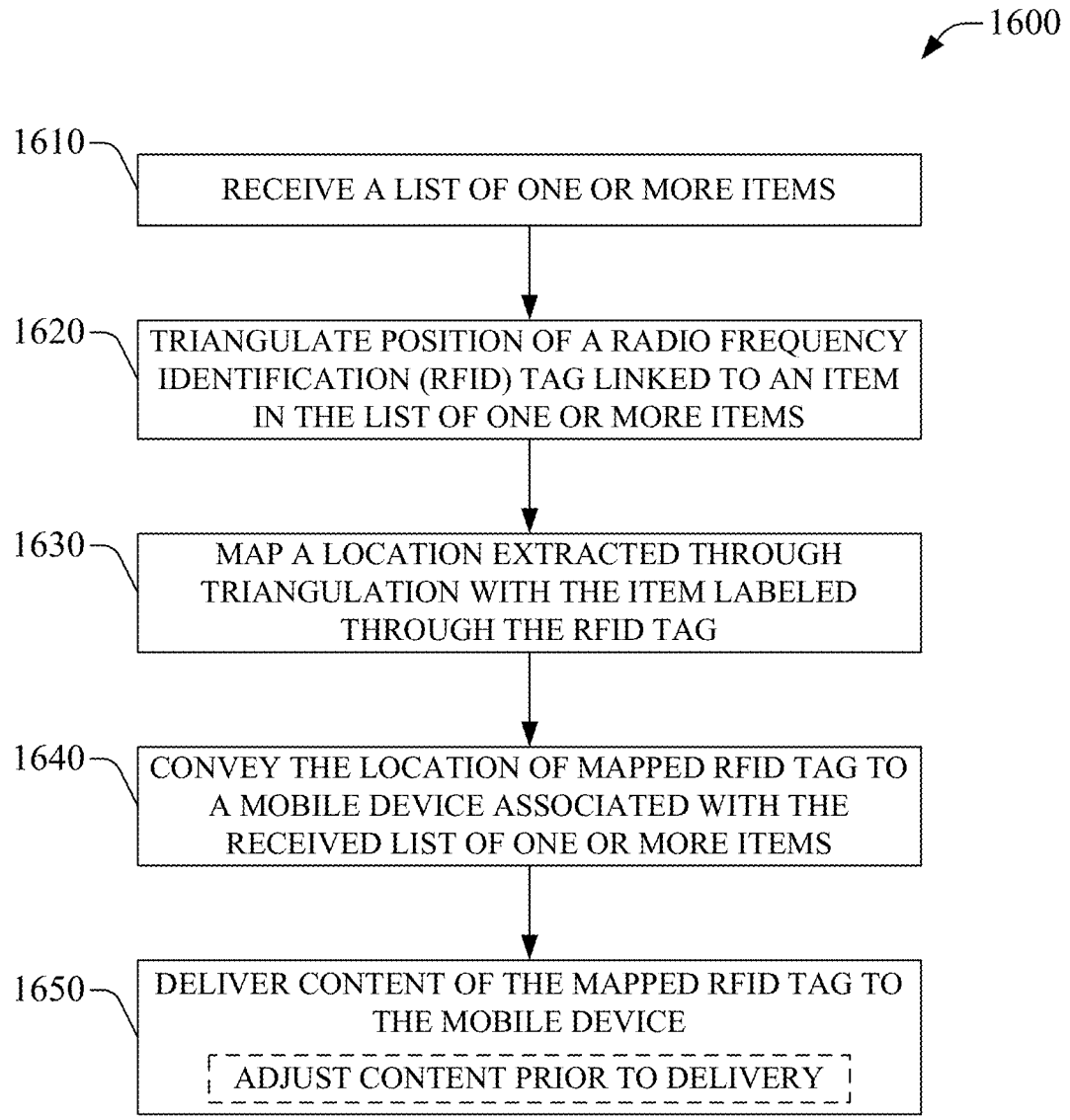
FIG. 16 displays a flowchart of an example method for associating an item with a mobile device according to aspects described herein.

FIG. 16 is a flowchart of an example method for associating an item with a mobile device according to aspects described herein. The subject example method can be effected by at least one of a femto AP or routing platform. In an aspect, one or more processors that confer functionality to the femto AP or the routing platform can implement, at least in part, the subject example method. At act 1610, a list of one or more items is received. At act 1620, position of an RFID tag linked to an item in the list of one or more items is triangulated. Triangulation of the position can be performed through TOF measurements based on at least one of a predetermined configurable timing advance, or timing information received through a GNSS receiver. At act 1630, a location extracted through triangulation is mapped to the item labeled through the RFID tag. At act 1640, the location of the mapped RFID tag is conveyed to a mobile device associated with the received list of one or more items; for instance, the mobile device can be linked to a subscriber that generated the list. In an aspect, a femto network platform relaying the list or a network external the femto network platform can exploit subscriber information to link unique identifier of the mobile device to credentials, e.g., password(s) or passkey(s), employed by the subscriber to access a service or application that enables generation of the list of one or more items. At act 1650, content of the mapped RFID tag is delivered to the mobile device. Delivering the content can include adjusting the content prior to delivery, such adjustment can allow to customize features of the content such as pricing of the item labeled through the RFID tag.

Figure 17:
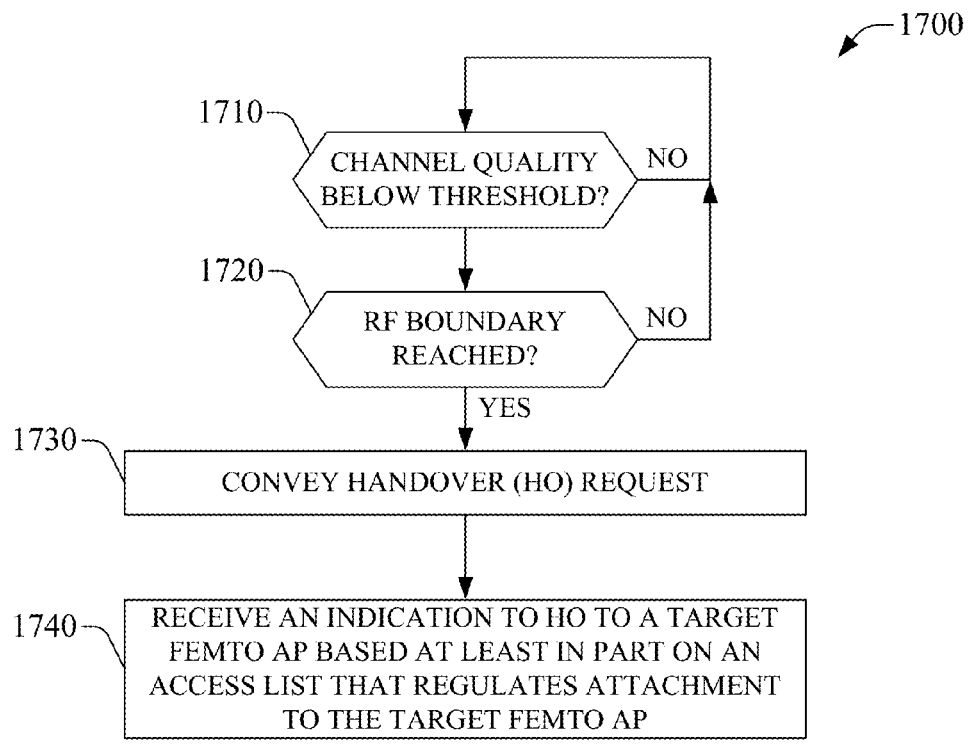
FIG. 17 represents a flowchart of an example method for handing off a mobile device within coverage areas within a femto enterprise network according to aspects described herein.

FIG. 17 is a flowchart of an example method for handing off a mobile device within coverage areas within a femto enterprise network according to aspects described herein. The subject example method can be effected by at least one of a femto AP or routing platform. In an aspect, at least one or more processor(s) that confer functionality to the femto AP or the routing platform can implement, at least in part, the subject example method 1700. At act 1710, it is evaluated if channel quality is below threshold. Channel quality can include FL and RL signal strength. In the negative case, evaluation is re-enacted. In the affirmative case, flow is directed to act 1720, in which it is probed whether an RF boundary is reached. A negative outcome results in flow being directed to act 1710. Conversely, a positive outcome results in conveying a handover request at act 1730. The RF boundary can be configurable and established in accordance at least in part with at least one of a schedule or one or more operation condition(s) of the femto enterprise network, wherein operation condition(s) can include at least one of network load such as number of served mobile devices; other-femto interference; available bandwidth; or channel quality. At act 1740, an indication to HO to a target femto AP is received based at least in part on an access list that regulated attachment to the target femto AP.

Figure 18:
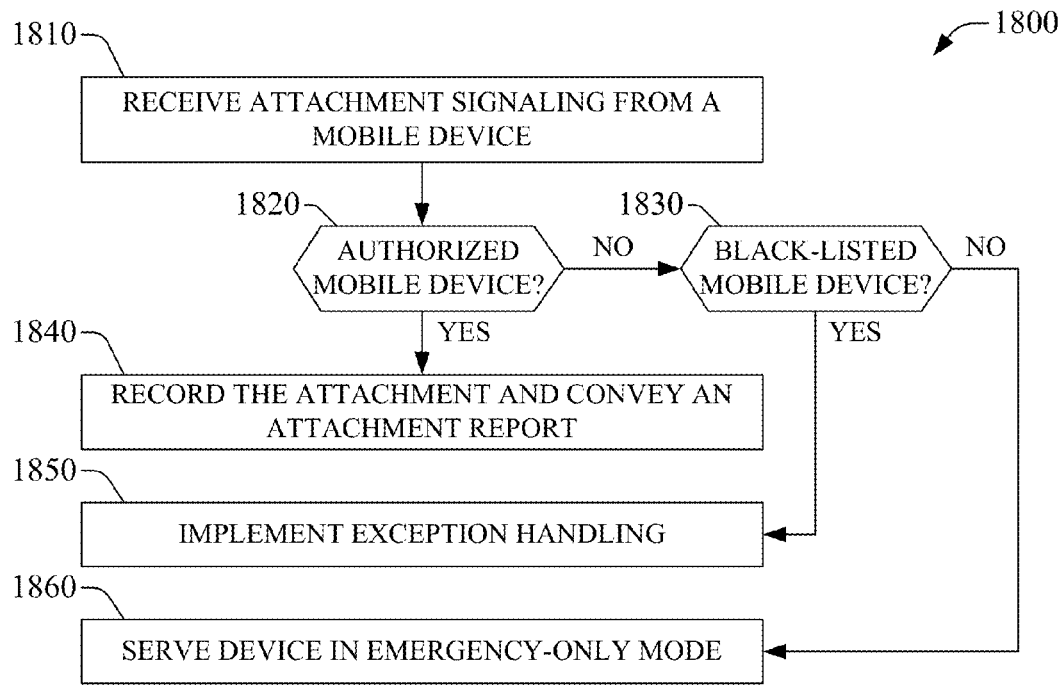
FIG. 18 displays a flowchart of an example method for signaling to a routing platform an attachment of a wireless device to a femto access point in a femto enterprise network according to aspects described herein.

FIG. 18 displays a flowchart of an example method 1800 for signaling to a routing platform an attachment of a wireless device to a femto access point in a femto enterprise network according to aspects described herein. A femto AP (e.g., femto 104₃) functionally linked to a routing platform (e.g., 110 or 510) in a femto enterprise network as described herein can enact, or implement the subject example method. In an aspect, at least one or more processor(s) that confer functionality to the femto AP can implement, at least in part, the subject example method 1800. At act 1810 attachment signaling is received from a mobile device, the attachment signaling can include wireless pilot signal(s) which can be conveyed when the mobile device operates in idle mode. At act 1820, it is determined if the mobile device is authorized to access service through a femto AP, which can be the femto AP that enacts the subject example method. Authorization or access privilege(s) can be determined by an access list, e.g., access list(s) 353, that regulates at least a level of service provide to user equipment through the femto AP. When the mobile device is authorized, the attachment is recorded, e.g., as part of access record(s) 355, and an attachment report is conveyed at act 1840. In an aspect, the attachment report can deliver registration information such as a time stamp, UE identifier codes or tokens, or the like. A conveyed attachment report can be aggregated at the routing platform functionally linked to the femto AP that can enact the subject example method. Conversely, when the mobile device is not authorized, flow is directed to act 1830 in which it is established whether the mobile device is a blacklisted device. In the affirmative case, exception handling is implemented at act 1850. Exception handling can include delivering an alarm, e.g., a SMS communication, a USSD code, an email message, an instant message, etc., to an authority such as a law-enforcement agency. In the negative case, the mobile device is served in emergency-mode only at act 1860.

Figure 19:
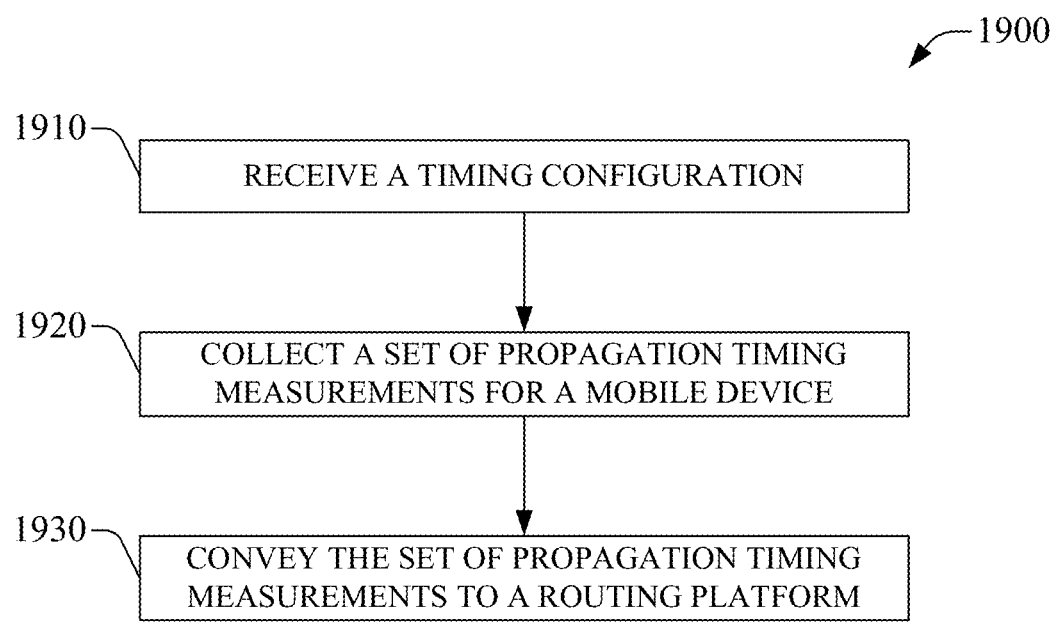
FIG. 19 is a flowchart of an example method for assisting localization of a mobile device that operates in the femto enterprise according to aspects described herein.

FIG. 19 is a flowchart of an example method 1900 for assisting localization of a mobile device that operates in the femto enterprise network according to aspects described herein. A femto AP (e.g., femto 104₃) functionally linked to a routing component (e.g., 110 or 510) in a femto enterprise network as described herein can enact, or implement the subject example method 1900. Alternatively or additionally, at least one or more processor(s) that confer functionality to the femto AP can implement, at least in part, the subject example method. At act 1910, a timing configuration is received. The timing configuration can synchronize time amongst a set of femto APs in a femtocell mesh network. In addition, the timing configuration can enable selection of a clock source, which can be part of a clock layer, e.g., 445, that determines a spatially resolution that can be attained through triangulation based at least in part on TOF measurements that can be effected by the femto AP the implements the subject example method. At act 1920, a set of propagation timing measurements is collected. The set includes one or more measurements. At act 1930, the set of timing measurements is conveyed to a routing platform. In an aspect, the routing platform can exploit timing data to generate a location estimate of a mobile device or an entity linked to an apparatus with wireless capability.

Figure 20:
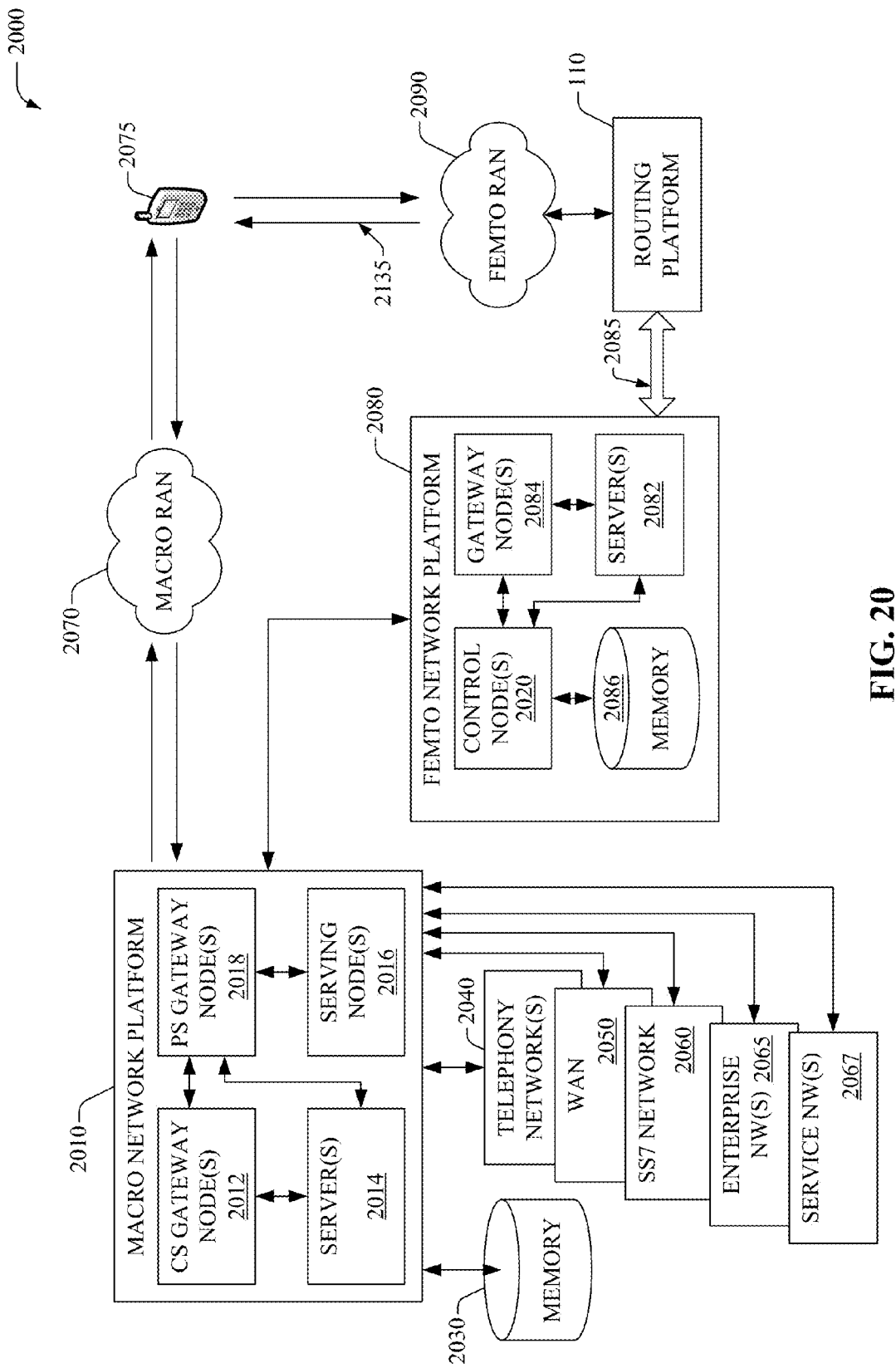
FIG. 20 illustrates an example wireless communication environment with associated components that can enable operation of a femtocell enterprise network in accordance with aspects described herein.

To provide further context for various aspects of the subject specification, FIG. 20 illustrates an example wireless communication environment 2000, with associated components that can enable operation of a femtocell enterprise network in accordance with aspects described herein. Wireless communication environment 2000 includes two wireless network platforms: (i) A macro network platform 2010 that serves, or facilitates communication) with user equipment 2075 via a macro radio access network (RAN) 2070. It should be appreciated that in cellular wireless technologies (e.g., 4G, 3GPP UMTS, HSPA, 3GPP LTE, 3GPP UMB), macro network platform 2010 is embodied in a Core Network. (ii) A femto network platform 2080, which can provide communication with UE 2075 through a femto RAN 2090, linked to the femto network platform 2080 through a routing platform 102 via backhaul pipe(s) 2085, wherein backhaul pipe(s) are substantially the same a backhaul link 1240. It should be appreciated that femto network platform 2080 typically offloads UE 2075 from macro network, once UE 2075 attaches (e.g., through macro-to-femto handover, or via a scan of channel resources in idle mode) to femto RAN.

It is noted that RAN includes base station(s), or access point(s), and its associated electronic circuitry and deployment site(s), in addition to a wireless radio link operated in accordance with the base station(s). Accordingly, macro RAN 2070 can comprise various coverage cells like cell 1205, while femto RAN 2090 can comprise multiple femto access points. As mentioned above, it is to be appreciated that deployment density in femto RAN 2090 is substantially higher than in macro RAN 2070.

Generally, both macro and femto network platforms 2010 and 2080 include components, e.g., nodes, gateways, interfaces, servers, or platforms, that facilitate both packet-switched (PS) (e.g., internet protocol (IP), frame relay, asynchronous transfer mode (ATM)) and circuit-switched (CS) traffic (e.g., voice and data) and control generation for networked wireless communication. In an aspect of the subject innovation, macro network platform 2010 includes CS gateway node(s) 2012 which can interface CS traffic received from legacy networks like telephony network(s) 2040 (e.g., public switched telephone network (PSTN), or public land mobile network (PLMN)) or a SS7 network 2060. Circuit switched gateway 2012 can authorize and authenticate traffic (e.g., voice) arising from such networks. Additionally, CS gateway 2012 can access mobility, or roaming, data generated through SS7 network 2060; for instance, mobility data stored in a VLR, which can reside in memory 2030. Moreover, CS gateway node(s) 2012 interfaces CS-based traffic and signaling and gateway node(s) 2018. As an example, in a 3GPP UMTS network, gateway node(s) 2018 can be embodied in gateway GPRS support node(s) (GGSN).

In addition to receiving and processing CS-switched traffic and signaling, gateway node(s) 2018 can authorize and authenticate PS-based data sessions with served (e.g., through macro RAN) wireless devices. Data sessions can include traffic exchange with networks external to the macro network platform 2010, like wide area network(s) (WANs) 2050; it should be appreciated that local area network(s) (LANs) can also be interfaced with macro network platform 2010 through gateway node(s) 2018. Gateway node(s) 2018 generates packet data contexts when a data session is established. To that end, in an aspect, gateway node(s) 2018 can include a tunnel interface (e.g., tunnel termination gateway (TTG) in 3GPP UMTS network(s); not shown) which can facilitate packetized communication with disparate wireless network(s), such as Wi-Fi networks. It should be further appreciated that the packetized communication can include multiple flows that can be generated through server(s) 2014. It is to be noted that in 3GPP UMTS network(s), gateway node(s) 2018 (e.g., GGSN) and tunnel interface (e.g., TTG) comprise a packet data gateway (PDG).

Macro network platform 2010 also includes serving node(s) 2016 that convey the various packetized flows of information or data streams, received through gateway node(s) 2018. As an example, in a 3GPP UMTS network, serving node(s) can be embodied in serving GPRS support node(s) (SGSN).

As indicated above, server(s) 2014 in macro network platform 2010 can execute numerous applications (e.g., location services, online gaming, wireless banking, wireless device management . . . ) that generate multiple disparate packetized data streams or flows, and manage (e.g., schedule, queue, format . . . ) such flows. Such application(s), for example can include add-on features to standard services provided by macro network platform 2010. Data streams can be conveyed to gateway node(s) 2018 for authorization/authentication and initiation of a data session, and to serving node(s) 2016 for communication thereafter. Server(s) 2014 can also effect security (e.g., implement one or more firewalls) of macro network platform 2010 to ensure network's operation and data integrity in addition to authorization and authentication procedures that CS gateway node(s) 2012 and gateway node(s) 2018 can enact. Moreover, server(s) 2014 can provision services from external network(s), e.g., WAN 2050, or Global Positioning System (GPS) network(s) (not shown). It is to be noted that server(s) 2014 can include one or more processor configured to confer at least in part the functionality of macro network platform 2010. To that end, the one or more processor can execute code instructions stored in memory 2030, for example.

In example wireless environment 2000, memory 2030 stores information related to operation of macro network platform 2010. Information can include business data associated with subscribers; market plans and strategies, e.g., promotional campaigns, business partnerships; operational data for mobile devices served through macro network platform; service and privacy policies; end-user service logs for law enforcement; and so forth. Memory 2030 can also store information from at least one of telephony network(s) 2040, WAN(s) 2050, or SS7 network 2060, enterprise NW(s) 2065, or service NW(s) 2067.

Femto gateway node(s) 2084 have substantially the same functionality as PS gateway node(s) 2018. Additionally, femto gateway node(s) 2084 can also include substantially all functionality of serving node(s) 2016. In an aspect, femto gateway node(s) 2084 facilitates handover resolution, e.g., assessment and execution. Further, control node(s) 2020 can receive handover requests and relay them to a handover component (not shown) via gateway node(s) 2084. According to an aspect, control node(s) 2020 can support RNC capabilities and can be substantially similar to the control component 320 (FIG. 3) and can include functionality thereof.

Server(s) 2082 have substantially the same functionality as described in connection with server(s) 2014. In an aspect, server(s) 2082 can execute multiple application(s) that provide service (e.g., voice and data) to wireless devices served through femto RAN 2090. Server(s) 2082 can also provide security features to femto network platform. In addition, server(s) 2082 can manage (e.g., schedule, queue, format . . . ) substantially all packetized flows (e.g., IP-based, frame relay-based, ATM-based) it generates in addition to data received from macro network platform 2010. It is to be noted that server(s) 2082 can include one or more processor configured to confer at least in part the functionality of macro network platform 2010. To that end, the one or more processor can execute code instructions stored in memory 2086, for example.

Memory 2086 can include information relevant to operation of the various components of femto network platform 2080. For example operational information that can be stored in memory 2086 can comprise, but is not limited to, subscriber information; contracted services; maintenance and service records; femto cell configuration (e.g., devices served through femto RAN 2090; access control lists, or white lists); service policies and specifications; privacy policies; add-on features; and so forth.

It is noted that femto network platform 2080 and macro network platform 2010 can be functionally connected through one or more reference link(s) or reference interface(s). In addition, femto network platform 2080 can be functionally coupled directly (not illustrated) to one or more of external network(s) 2040, 2050, 2060, 2065 or 2067. Reference link(s) or interface(s) can functionally link at least one of gateway node(s) 2084 or server(s) 2086 to the one or more external networks 2040, 2050, 2060, 2065 or 2067.

Figure 21:
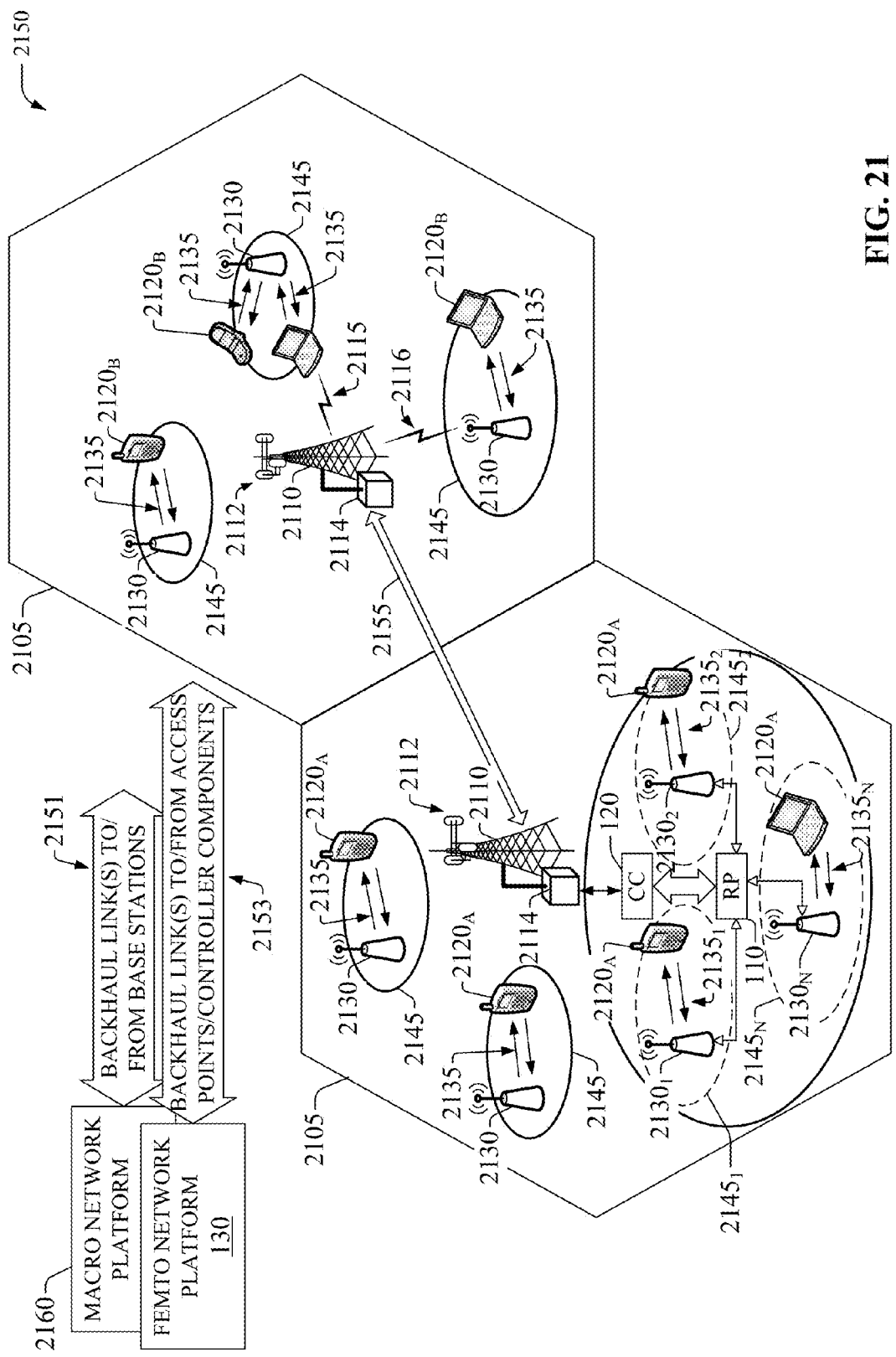
FIG. 21 illustrates a schematic deployment of a macro cell and a femto cell for wireless coverage in accordance with aspects of the subject specification.

FIG. 21 illustrates a wireless environment that includes macro cells and femtocells for wireless coverage in accordance with aspects described herein. In wireless environment 2150, two areas 2105 represent "macro" cell coverage, each macro cell is served by a base station 2110. It can be appreciated that macro cell coverage area 2105 and base station 2110 can include functionality, as more fully described herein, for example, with regard to system 2100. Macro coverage is generally intended to serve mobile wireless devices, like UE $2120_A$, $2120_B$, in outdoors locations. An over-the-air wireless link 115 provides such coverage, the wireless link 1215 comprises a downlink (DL) and an uplink (UL), and utilizes a predetermined band, licensed or unlicensed, of the radio frequency (RF) spectrum. As an example, UE $2120_A$, $2120_E$ can be a 3GPP Universal Mobile Telecommunication System (UMTS) mobile phone. It is noted that a set of base stations, its associated electronics, circuitry or components, base stations control component(s), and wireless links operated in accordance to respective base stations in the set of base stations form a radio access network (RAN). In addition, base station 2110 communicates via backhaul link(s) 2151 with a macro network platform 2160, which in cellular wireless technologies (e.g., 3rd Generation Partnership Project (3GPP) Universal Mobile Telecommunication System (UMTS), Global System for Mobile Communication (GSM)) represents a core network.

In an aspect, macro network platform 2160 controls a set of base stations 2110 that serve either respective cells or a number of sectors within such cells. Base station 2110 comprises radio equipment 2114 for operation in one or more radio technologies, and a set of antennas 2112 (e.g., smart antennas, microwave antennas, satellite dish(es)...) that can serve one or more sectors within a macro cell 2105. It is noted that a set of radio network control node(s), which can be a part of macro network platform; a set of base stations (e.g., Node B 2110) that serve a set of macro cells 2105; electronics, circuitry or components associated with the base stations in the set of base stations; a set of respective OTA wireless links (e.g., links 2115 or 2116) operated in accordance to a radio technology through the base stations; and backhaul link(s) 2155 and 2151 form a macro radio access network (RAN). Macro network platform 2160 also communicates with other base stations (not shown) that serve other cells (not shown). Backhaul link(s) 2151 or 2153 can include a wired backbone link (e.g., optical fiber backbone, twisted-pair line, T1/E1 phone line, a digital subscriber line (DSL) either synchronous or asynchronous, an asymmetric ADSL, or a coaxial cable ...) or a wireless (e.g., line-of-sight (LOS) or non-LOS) backbone link. Backhaul pipe(s) 2155 link disparate base stations 2110. According to an aspect, backhaul link 2153 can connect multiple femto access points 2130 and/or controller components (CC) 120 to the femto network platform 130. In one example, multiple femto APs can be connected to a routing platform (RP) 110, which in turn can be connect to a controller component (CC) 120. Typically, the information from UEs $2120_A$ can be routed by the RP 102, for example, internally, to another UE $2120_A$ connected to a disparate femto AP connected to the RP 110, or, externally, to the femto network platform 130 via the CC 120, as discussed in detail supra.

In wireless environment 2150, within one or more macro cell(s) 2105, a set of femtocells 2145 served by respective femto access points (APs) 2130 can be deployed. It can be appreciated that, aspects of the subject innovation are geared to femtocell deployments with substantive femto AP density, e.g., $10^4$-$10^7$ femto APs 2130 per base station 2110. According to an aspect, a set of femto access points $2130_1$-$2130_N$, with N a natural number, can be functionally connected to a routing platform 102, which can be functionally coupled to a controller component 120. The controller component 120 can be operationally linked to the femto network platform 330 by employing backhaul link(s) 2153. Accordingly, UEs UE $2120_A$ connected to femto APs $2130_1$-$2130_N$ can communicate internally within the femto enterprise via the routing platform (RP) 110 and/or can also communicate with the femto network platform 330 via the RP 110, controller 120 and the backhaul link(s) 2153. It can be appreciated that although only one femto enterprise is depicted in FIG. 21, multiple femto enterprise networks can be deployed within a macro cell 2105.

It is noted that while various aspects, features, or advantages described herein have been illustrated through femto access point(s) and associated femto coverage, such aspects and features also can be exploited for home access point(s) (HAPs) that provide wireless coverage through substantially any, or any, disparate telecommunication technologies, such as for example Wi-Fi (wireless fidelity) or picocell telecommunication. Additionally, aspects, features, or advantages of the subject innovation can be exploited in substantially any wireless telecommunication, or radio, technology; for example, Wi-Fi, Worldwide Interoperability for Microwave Access (WiMAX), Enhanced General Packet Radio Service (Enhanced GPRS), 3GPP LTE, 3GPP2 UMB, 3GPP UMTS, HSPA, HSDPA, HSUPA, or LTE Advanced. Moreover, substantially all aspects of the subject innovation can include legacy telecommunication technologies.

Various aspects or features described herein can be implemented as a method, apparatus, or article of manufacture using standard programming and/or engineering techniques. In addition, various aspects disclosed in the subject specification can also be implemented through program modules stored in a memory and executed by a processor, or other combination of hardware and software, or hardware and firmware. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips ...), optical disks (e.g., compact disc (CD), digital versatile disc (DVD), blu-ray disc (BD) ...), smart cards, and flash memory devices (e.g., card, stick, key drive ...). Additionally it should be appreciated that a carrier wave can be employed to carry computer-readable electronic data such as those used in transmitting and receiving electronic mail or in accessing a network such as the internet or a local area network (LAN). Of course, those skilled in the art will recognize many modifications may be made to this configuration without departing from the scope or spirit of the claimed subject matter.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor also can be implemented as a combination of computing processing units.

In the subject specification, terms such as "store," "data store," "data storage," "database," "repository," and substantially any other information storage component relevant to operation and functionality of a component, refer to "memory components," or entities embodied in a "memory" or components comprising the memory. It will be appreciated that the memory components described herein can be either volatile memory or nonvolatile memory, or can include both volatile and nonvolatile memory. In addition, memory components or memory elements can be removable or stationary. Moreover, memory can be internal or external to a device or component, or removable or stationary. Memory can include various types of media that are readable by a computer, such as hard-disc drives, zip drives, magnetic cassettes, flash memory cards or other types of memory cards, cartridges, or the like.

By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory What has been described above includes examples of systems and methods that provide advantages of the subject innovation. It is, of course, not possible to describe every conceivable combination of components or methodologies for purposes of describing the subject innovation, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:
   a memory to store executable instructions; and
   a processor, coupled to the memory, that facilitates execution of the executable instructions to perform operations, comprising:
   in response to determining that a vehicle has been parked, instructing a set of femto access point devices to determine range estimate data associated with a device coupled to the vehicle, wherein the set of femto access point devices is linked via a routing platform device,
   based on the range estimate data, determining location data indicative of a location estimate for the device, and
   in response to determining that a user equipment related to the device has entered a coverage area associated with a femto access point device of the set of femto access point devices, facilitating a transmission of the location data to the user equipment via the femto access point device.

2. The system of claim 1, wherein the range estimate data is determined by the set of femto access point devices based on timing configuration data that configures a granularity associated with a resolution of the location estimate and wherein the operations further comprise:
   controlling the timing configuration data to adjust the granularity.

3. The system of claim 2, wherein the timing configuration data specifies a clock source that provides a defined timing advance.

4. The system of claim 1, wherein the facilitating comprises facilitating the transmission via a text message.

5. The system of claim 1, wherein the facilitating comprises facilitating the transmission in response to determining that request data indicative of a request for the location data has been received.

6. The system of claim 5, wherein the request data comprises code data indicative of an unstructured supplementary service data code.

7. The system of claim 1, wherein the transmission is a first transmission, the device is a first device, and the operations further comprise:
   in response to determining that identifier data associated with the first device matches information within a data structure associated with a law enforcement agency, facilitating a second transmission of the location data to a second device associated with the law enforcement agency.

8. The system of claim 7, wherein the coverage area is a first coverage area and the operations further comprise:
   in response to the determining that the identifier data matches the information, tracking motion of the first device within a second coverage area of the set of femto access point devices.

9. The system of claim 3, wherein the determining the location data comprises determining width data associated with a time-of-flight band that is determined using the defined timing advance.

10. A method, comprising:
    directing, by a routing platform device comprising a processor, instruction data to a set of femto access point devices linked via the routing platform device, wherein the instruction data requests the set of femto access point devices to determine, in response to determining that a vehicle has been parked within a coverage area of the set of femto access point devices, range estimate data associated with a device coupled to the vehicle;
    receiving, by the routing platform device, range estimate data from the set of femto access point devices to facilitate determining location data indicative of a location estimate for the device; and
    in response to determining that a user equipment linked to the device has entered the coverage area, directing, by the routing platform device, the location data to the user equipment via a femto access point device of the set of femto access point devices.

11. The method of claim 10, further comprising:
    adjusting, by the routing platform device, timing configuration data that is employed by the set of femto access point devices to facilitate determining of the range estimate data, wherein the adjusting comprises adjusting the timing configuration data to configure a granularity associated with a resolution of the location estimate.

12. The method of claim 11, wherein the adjusting comprises selecting a clock source that is to be employed by the set of femto access point devices to facilitate the determining of the range estimate data.

13. The method of claim 12, wherein the determining the location data comprises determining width data associated with a time-of-flight band that is determined based on a timing advance established by the clock source.

14. The method of claim 10, further comprising:
    receiving, by the routing platform device, request data indicative of a request for the location data from the user equipment, wherein the directing comprises directing the location data in response to the receiving the request data.

15. The method of claim 14, wherein the receiving the request data comprises receiving the request data via a text message.

16. The method of claim 14, wherein the receiving the request data comprises receiving code data indicative of an unstructured supplementary service data code.

17. A computer readable storage device comprising executable instructions that, in response to execution, cause a system comprising a processor to perform operations, comprising:
    receiving range estimate data that is determined based on signaling between a set of femto access point devices and a device coupled to a vehicle located within a coverage area associated with the set of femto access point devices, wherein the set of femto access point devices are coupled via a routing platform device and wherein the range estimate data is determined based on determining that the vehicle has been parked; and based on the range estimate data, determining location data indicative of a location estimate for the device, wherein the location data is transferred from the routing platform device to a user equipment related to the device in response to determining that the user equipment has registered with a femto access point device of the femto access point devices.

18. The tangible computer readable storage device of claim 17, wherein the operations further comprise:
modifying timing configuration data employed by the set of femto access point devices to facilitate a determination of the range estimate data, wherein the timing configuration data specifies a granularity associated with a resolution of the location estimate.

19. The computer readable storage device of claim 18, wherein the modifying the timing configuration data comprises specifying a clock source that is to be employed by the set of femto access point devices to facilitate the determining of the range estimate data.

20. The computer readable storage device of claim 17, wherein the range estimate data comprises time of flight measurement data that is determined based on a configurable timing advance.

* * * * *